(12) United States Patent
Aoki et al.

(10) Patent No.: US 7,905,596 B2
(45) Date of Patent: Mar. 15, 2011

(54) FUNDUS OBSERVATION DEVICE, AN OPHTHALMOLOGIC IMAGE PROCESSING UNIT, AN OPHTHALMOLOGIC IMAGE PROCESSING PROGRAM, AND AN OPHTHALMOLOGIC IMAGE PROCESSING METHOD

(75) Inventors: Hiroyuki Aoki, Tokyo (JP); Takashi Fujimura, Tokyo (JP); Yasufumi Fukuma, Tokyo (JP); Hisashi Tsukada, Tokyo (JP); Tsutomu Kikawa, Tokyo (JP)

(73) Assignee: Kabushiki Kaisha Topcon, Tokyo (JP)

( * ) Notice: Subject to any disclaimer, the term of this patent is extended or adjusted under 35 U.S.C. 154(b) by 241 days.

(21) Appl. No.: 11/760,314

(22) Filed: Jun. 8, 2007

(65) Prior Publication Data
US 2007/0285619 A1    Dec. 13, 2007

(30) Foreign Application Priority Data
Jun. 9, 2006    (JP) ................................. 2006-160896

(51) Int. Cl.
*A61B 3/14*    (2006.01)
*A61B 3/10*    (2006.01)
*A61B 3/00*    (2006.01)

(52) U.S. Cl. .......................... 351/206; 351/221; 351/246

(58) Field of Classification Search .................. 351/206, 351/221; 396/18
See application file for complete search history.

(56) References Cited

U.S. PATENT DOCUMENTS

| 7,347,548 B2 * | 3/2008 | Huang et al. .................. 351/205 |
| 2006/0119858 A1 | 6/2006 | Knighton |
| 2007/0070295 A1 * | 3/2007 | Tsukada et al. ............... 351/206 |
| 2007/0159596 A1 * | 7/2007 | Fukuma et al. ............... 351/206 |
| 2007/0195269 A1 * | 8/2007 | Wei et al. ...................... 351/221 |
| 2007/0222945 A1 * | 9/2007 | Tsukada et al. ............... 351/205 |

FOREIGN PATENT DOCUMENTS

| JP | 2003-000543 | 1/2003 |
| JP | 2004-350849 | 12/2004 |
| JP | 2005-241464 | 9/2005 |

OTHER PUBLICATIONS

Wojtkowski et al: "Three-dimensional Retinal Imaging with High-Speed Ultrahigh-Resolution Optical Coherence Tomography"—Ophthalmology, J. B. Lippincott Co., Philadelphia, PA, US., vol. 112, No. 10, Oct. 2005, pp. 1734-1746, OP005104095; ISSN: 0161-6420; *figures 2f.2j* *p. 173*.
Extended European Search Report—EP 07 01 0818.

* cited by examiner

*Primary Examiner* — Jordan M. Schwartz
(74) *Attorney, Agent, or Firm* — Edwards Angell Palmer & Dodge LLP

(57) ABSTRACT

First image forming part forms a two-dimensional surface image of a fundus oculi of an eye based on optically obtained data. Second image forming part forms tomographic images of fundus oculi based on data obtained by optically scanning a region of the surface of fundus oculi corresponding to at least part of two-dimensional image. Accumulated image generating part generates an accumulated image by accumulating the formed tomographic images in a depth-wise direction. Extracting part extracts first vascular territory corresponding to a fundus oculi vessel from two-dimensional image formed by first image forming part, and also extracts second vascular territory corresponding to a fundus oculi vessel from accumulated image generated by accumulated image generating part. Specification part specifies a position of a vascular cross sectional region corresponding to a cross section of a fundus oculi vessel in the tomographic image based on extracted first vascular territory and extracted second vascular territory.

13 Claims, 20 Drawing Sheets

PRIOR ART

PRIOR ART

FUNDUS OBSERVATION DEVICE, AN OPHTHALMOLOGIC IMAGE PROCESSING UNIT, AN OPHTHALMOLOGIC IMAGE PROCESSING PROGRAM, AND AN OPHTHALMOLOGIC IMAGE PROCESSING METHOD

BACKGROUND OF THE INVENTION

1. Field of the Invention

The present invention relates to a fundus observation device for observing the state of the fundus oculi of an eye, an opthalmologic image processing unit, an opthalmologic image processing program, and an opthalmologic image processing method.

2. Description of the Related Art

As a fundus observation device, conventionally, a fundus camera has been widely used. FIG. 19 shows one example of the appearance of a conventional, general fundus camera. FIG. 20 shows one example of a composition of an optical system internally accommodated in a fundus camera (e.g. JP Patent laid-open No. 2004-350849). Here, "observation" includes at least a case in which produced fundus images are observed (fundus observations with the naked eye may be included).

First, referring to FIG. 19, an explanation is made regarding the appearance of a conventional fundus camera 1000. This fundus camera 1000 is provided with a platform 3 mounted on a base 2 slidably in the front and rear, right and left directions (horizontal direction). On this platform 3, an operation panel 3a and a control lever 4 are installed for an examiner to conduct various operations.

The examiner may move the platform 3 three-dimensionally on the base 2 by operating the control lever 4. On the top of the control lever 4, an operation button 4a is installed, which is pressed down to obtain fundus oculi images.

On the base 2, a post 5 is installed standing upwards. On the post 5, a jaw rest 6 where the jaw of a patient is to be rested and an external fixation lamp 7 as a light source for fixing an eye E are provided.

On the platform 3, a main body part 8 is installed to accommodate various optical systems or control systems of the fundus camera 1000. Furthermore, the control system may be installed inside the base 2 or the platform 3, etc., or in an external device such as a computer, etc. connected to the fundus camera 1000.

On the side of the eye E of the main body part 8 (the left side of the page in FIG. 19), an objective lens part 8a disposed opposite the eye E is installed. Also, on the examiner's side of the main body part 8 (the right side of the page in FIG. 19, an eyepiece part 8b for observing the fundus oculi of the eye E with the naked is installed.

Furthermore, connected to the main body part 8 is a still camera 9 for producing a still image of a fundus oculi of the eye E and an imaging device 10 such as a TV camera, etc. for producing still images or moving images of a fundus oculi. The still camera 9 and the imaging device 10 are formed removably with respect to the main body part 8.

As a still camera 9, in accordance with various conditions such as the purpose of an examination or the saving method of produced images, etc., a digital camera equipped with imaging elements such as CCD (Charge Coupled Device) or CMOS (Complementary Metal Oxide Semiconductor), a film camera, and an instant camera, etc. may interchangeably be used when it is appropriate. The main body part 8 is equipped with a mounting part 8c for interchangeably mounting such a still camera 9.

If the still camera 9 or the imaging device 10 is for taking digital images, the image data of the produced fundus image may be sent to a device such as a computer, etc. connected to the fundus camera 1000 and be observed as a fundus image by being displayed on the display. Also, the image data can be sent to an image storing device connected to the fundus camera 1000 to compile a database and be used as electronic data for creating electronic medical charts, etc.

Furthermore, on the examiner's side of the main body part 8, a touch panel monitor 11 is installed. On this touch panel monitor 11, fundus images of the eye E created based on the video signals output from the still camera 9 (of digital type) or the imaging device 10 are displayed. Moreover, on the touch panel monitor 11, the two-dimensional coordinate system with the center of the screen as the origin is displayed overlapped with a fundus image. When the screen is touched by the examiner at a desired position, the coordinate value corresponding to the touched position is displayed.

Next, referring to FIG. 20, a composition of an optical system of the fundus camera 1000 is described. Before imaging of a fundus oculi Ef of the eye E, the optical system of the fundus camera 1000 is aligned with the fundus oculi Ef (that is, the optical system is placed at a suitable position for imaging by moving the optical system in the x, y, and z directions as shown in FIG. 20). The optical system of the fundus camera 1000 is provided with an illuminating optical system 100 to light the fundus oculi Ef of the eye E, an imaging optical system 120 to guide the fundus reflection light of the illumination light to the eyepiece part 8b, the still camera 9, and the imaging device 10.

The illuminating optical system 100 comprises: an observation light source 101, a condenser lens 102, an imaging light source 103, a condenser lens 104, exciter filters 105 and 106, a ring transparent plate 107, a mirror 108, a liquid crystal display (LCD) 109, an illumination diaphragm 110, a relay lens 111, an aperture mirror 112, and an objective lens 113.

The observation light source 101 consists of a halogen lamp, etc. and emits continuous light for observing the fundus oculi. The condenser lens 102 is an optical element that converges the continuous light (observation illumination light) emitted by the observation light source 101 and substantially evenly irradiates the observation illumination light to the fundus oculi.

The imaging light source 103 consists of a xenon lamp, etc. to be flashed at the time of production of fundus oculi Ef images. The condenser lens 104 is an optical element that converges the flash light (imaging illumination light) emitted by the imaging light source 103 and irradiates the fundus oculi Ef evenly with the imaging illumination light.

The exciter filters 105 and 106 are filters to be used when fluorography of images of the fundus oculi Ef takes a place. The exciter filters 105 and 106 respectively can be inserted to and removed from the optical path by a drive mechanism (not illustrated) such as a solenoid, etc. The exciter filter 105 is disposed on the optical path in the event of FAG (fluorescein angiography). Whereas, the exciter filter 106 is disposed on the optical path in the event of ICG (indocyanine green angiography). Furthermore, when color images are being obtained, both the exciter filters 105 and 106 are retracted from the optical path.

The ring transparent plate 107 is disposed in a conjugating location with a pupil of the eye E, and is equipped with a ring transparent part 107a taking an optical axis of the illuminating optical system 100 as a center. The mirror 108 reflects the illumination light emitted by the observation light source 101 or by the imaging light source 103 in the direction of the optical axis of the imaging optical system 120. The LCD 109 displays a fixation target (not illustrated) for fixing the eye E.

The illumination diaphragm 110 is a diaphragm member to shut out a part of the illumination light for prevention of flare, etc. This illumination diaphragm 110 is composed movably in the light axial direction of the illuminating optical system 100, thereby being capable of changing the illuminating region of the fundus oculi Ef.

The aperture mirror 112 is an optical element to combine an optical axis of the illuminating optical system 100 and an optical axis of the imaging optical system 120. In the center region of the aperture mirror 112, an aperture part 112a is opened. The optical axis of the illuminating optical system 100 and the optical axis of the imaging optical system 120 are to be crossed at a substantially central location of the aperture part 112a. The objective lens 113 is installed in the objective lens part 8a of the main body part 8.

The illuminating optical system 100 having such a composition illuminates the fundus oculi Ef in the following manner. First, during fundus observation, the observation light source 101 is lit, and the observation illumination light is emitted. This observation illumination light irradiates the ring transparent plate 107 through the condenser lenses 102 and 104. (The exciter filters 105 and 106 are retracted from the optical path.) The light passed through the ring transparent part 107a of the ring transparent plate 107 is reflected by the mirror 108, passed though the LCD 109, the illumination diaphragm 110 and the relay lens 111, and reflected by the aperture mirror 112. The observing illumination light reflected by the aperture mirror 112 advances in the optical axial direction of the imaging optical system 120 and is converged by the objective lens 113, thereby entering the eye E and illuminating the fundus oculi Ef.

At this moment, the ring transparent plate 107 is disposed in a conjugating location with the pupil of the eye E, and a ring-shaped image of the observation illumination light entering the eye E is formed on the pupil. The fundus reflection light of the observation illumination light is to be emitted from the eye E through a central dark part of the ring-shaped image on the pupil. Thus, an effect of the observation illumination light entering the eye E on the fundus reflection light of the observation illumination light is prevented.

On the other hand, at the time of imaging of the fundus oculi Ef, flush light is emitted from the imaging light source 103 and the imaging illumination light is irradiated onto the fundus oculi Ef through the same path. In the case of fluorography, either the exciter filter 105 or the exciter filter 106 is disposed selectively on the optical path depending on whether FAG imaging or ICG imaging is carried out.

The imaging optical system 120 comprises: the objective lens 113, the aperture mirror 112 (the aperture part 112a thereof), an imaging diaphragm 121, barrier filters 122 and 123, a variable magnifying lens 124, a relay lens 125, an imaging lens 126, a quick return mirror 127 and an imaging media 9a. Herein, the imaging media 9a is an arbitrary imaging media (image pick-up elements such as CCD, camera film, instant film, etc.) used for the still camera 9.

The fundus reflection light of the illumination light, emitted through the central dark part of the ring-shaped image formed on the pupil from the eye E, enters the imaging diaphragm 121 through the aperture part 112a of the aperture mirror 112. The aperture mirror 112 reflects cornea reflection light of the illumination light, thereby acting so as not to mix the cornea reflection light into the fundus reflection light entering the imaging diaphragm 121. As a result, generation of flare on the observation images and/or produced images is prevented.

The imaging diaphragm 121 is a plate-shaped member at which plural circular light transparent parts of different sizes are formed. The plural light transparent parts constitute different diaphragms with different diaphragm values (F values), and are to be disposed alternatively on the optical path by a drive mechanism (not illustrated).

The barrier filters 122 and 123 can be inserted to and removed from the optical path by a drive mechanism (not illustrated) such as a solenoid, etc. In the event of FAG imaging, the barrier filter 122 is disposed on the optical path. Whereas in the event of ICG imaging, the barrier filter 123 is disposed onto the optical path. Furthermore, at the time of production of color images, both the barrier filters 122 and 123 are to be retracted from the optical path.

The variable magnifying lens 124 is to be movable in the light axial direction of the imaging optical system 120 by a drive mechanism (not illustrated). This makes it possible to change the magnifying ratio in observation and the magnifying ratio in imaging, and to focus images of a fundus oculi. The imaging lens 126 is a lens to focus the fundus reflection light from the eye E on the imaging media 9a.

The quick return mirror 127 is disposed rotatably around a rotary shaft 127a by a drive mechanism not illustrated herein. At the time of imaging of a fundus oculi Ef with the still camera 9, the fundus reflection light is supposed to be guided to the imaging media 9a by springing up the quick return mirror 127 that is obliquely mounted on the optical path. Whereas, at the time of imaging of a fundus oculi with the imaging device 10 or observation of a fundus oculi with the naked eye of the examiner, the quick return mirror 127 is to be obliquely mounted on the optical path to upwardly reflect the fundus reflection light.

The imaging optical system 120 is further provided, for guiding the fundus reflection light reflected by the quick return mirror 127, with a field lens 128, a switching mirror 129, an eyepiece 130, a relay lens 131, a reflection mirror 132, an imaging lens 133 and an image pick-up element 10a. The image pick-up element 10a is an image pick-up element such as CCD, etc. installed internally in the imaging device 10. On the touch panel monitor 11 a fundus oculi image Ef' imaged by the image pick-up element 10a is be displayed.

The switching mirror 129 is to be rotatable around a rotary shaft 129a in the same manner as the quick return mirror 127. This switching mirror 129 is obliquely disposed on the optical path during observation with the naked eye and guides the light reflected on the fundus oculi to the eyepiece 130.

Also, when a fundus image is formed by using the imaging device 10, the switching mirror 129 is retracted from the optical path, and the fundus reflection light is guided toward the image pick-up element 10a. In this case, the fundus reflection light is directed toward a relay lens 131, is reflected by the mirror 132, and is focused on the image pick-up element 10a by the imaging lens 133.

The fundus camera 1000 is a fundus observation device to be used for observing the state of the surface of the fundus oculi Ef, that is, the retina. In other words, the fundus camera 1000 is a fundus observation device to obtain a two-dimensional fundus oculi image when the fundus oculi Ef is seen from the corneal direction onto the eye E. On the other hand, in the deep layer of retina, tissues such as the choroidea and sclera exist, and a technology for observing these deep layer tissues has been desired. In recent years, devices for observing these deep layer tissues have been practically implemented (e.g. JP Patent laid-open No. 2003-00543, JP Patent laid-open No. 2005-241464).

The fundus observation devices disclosed in JP Patent laid-open No. 2003-00543 and JP Patent laid-open No. 2005-

241464 are devices to which so-called OCT (Optical Coherence Tomography) technology is applied, which are called an optical coherence tomography device. The fundus observation device is a device that, by splitting low coherence light into two to guide one (signal light) of the split lights to the fundus oculi and the other (reference light) to a given reference object, and detecting and analyzing interference light obtained by overlaying the signal light reflected by the fundus oculi and the reference light reflected by the reference object, forms a tomographic image of the surface of the fundus oculi or the deep layer tissue. The optical coherence tomography device is capable of forming a three-dimensional image of the fundus oculi based on plural tomographic images. The optical coherence tomography device disclosed in JP Patent laid-open No. 2003-00543 is generally called a Fourier domain OCT.

The Fourier domain OCT is designed to form a tomographic image having a cross-section in the depth direction (the z-direction in FIG. 20) along a scanning line by scanning and irradiating the fundus oculi with the signal light. Such scanning with the signal light is referred to as B-scan (see NEDO Workshop "Seeing (examining) inside the body from the 'window' of the human body, the fundus oculi"—Development of an ultra early diagnostic device for lifestyle-related diseases using the latest optical technologies (held on Apr. 25, 2005), Internet<URL:http://www.nedo.go.jp/informations/koubo/170627_2/besshi 3.pdf>).

In the case of formation of a three-dimensional image, B-scan is performed along a plurality of scanning lines, and an interpolation process is applied to the resulting plurality of tomographic images for the generation of three-dimensional image data. This three-dimensional image data is referred to as volume data, voxel data, etc. as in medical imaging diagnosis devices such as an X-ray CT device, and is image data of a form in which pixel data (data of brightness, contrasting density, color and so on including a luminance value and a RGB value) is assigned to respective voxels arranged three-dimensionally. A three-dimensional image is displayed as a pseudo three-dimensional image seen from a specified viewing angle obtained by rendering volume data.

There has been a problem such that the state of the layer boundary of the fundus oculi (e.g. retina) cannot be visually identified because the image region directly under the fundus oculi vessel (the position in the +z direction shown in FIG. 20) becomes unclear when tomographic images of the fundus oculi are captured with the conventional optical image measuring apparatus.

For example, as shown in FIG. 21, when there is (a tomographic image of) a fundus oculi vessel V in (an image of) a layer L1' in the tomographic image G' of the fundus oculi, an image region V' located directly under the fundus oculi vessel V becomes unclear due to the effect of the fundus oculi vessel V, and there is a case where the state of a boundary g2' between the layer L1' and a layer L2', the state of a boundary g3' between the layer L2' and a layer L3', and the state of the boundary g4' between the layer L3' and a layer thereunder (not shown) cannot be ascertained. As a result, the thickness of each of the layers L1', L2', L3', etc., directly under the fundus oculi vessel V cannot be measured. Therefore, the thickness of the layer at such position is recorded as "0", "immeasurable", or the like, and there is a problem such that it is impossible to measure the thickness of the layer over the entire region where the image is captured.

When a user searches such image region V' by visually identifying the tomographic image G', considerable time and labor is required, and therefore, it may not be practical in use. In addition, it is difficult to automatically extract the image region V' from within the tomographic image G' because it is difficult to specify the fundus oculi vessel V by analyzing the tomographic image G' (although the fundus oculi vessel V is shown for illustrative purpose in FIG. 21, it is generally impossible to clearly specify the actual fundus oculi vessel as in the above manner). Symbol LS in FIG. 21 represents the signal light (described above) illuminated onto the fundus oculi Ef from the optical image measuring apparatus.

SUMMARY OF THE INVENTION

The present invention is made to solve such problems, and an object thereof is to provide a fundus observation device, an opthalmologic image processing unit, an opthalmologic image processing program, and an opthalmologic image processing method that make it possible to ascertain the position of an image region corresponding to a cross section of a vessel in a tomographic image of a fundus oculi (a vascular cross sectional region).

Further, another object of the present invention is to provide a fundus observation device, an opthalmologic image processing unit, an opthalmologic image processing program, and an opthalmologic image processing method that make it possible to obtain an image region of a layer that is located directly under a vascular cross sectional region in a tomographic image of a fundus oculi (a layer region) and obtain an image region of the boundary between layers (a boundary region).

Furthermore, another object of the present invention is to provide a fundus observation device, an opthalmologic image processing unit, an opthalmologic image processing program, and an opthalmologic image processing method that make it possible to measure the thickness of a layer region directly under a vascular cross sectional region.

In order to achieve the above purposes, in the first aspect of the present invention, a fundus observation device comprises: a first image forming part configured to form a two-dimensional image of the surface of the fundus oculi of an eye based on optically captured data; a second image forming part configured to form tomographic images of said fundus oculi based on data captured by optically scanning the region of the surface of the fundus oculi corresponding to at least part of the two-dimensional image; an accumulated image forming part configured to generate accumulated images by accumulating the formed tomographic images in the depth-wise direction; an extracting part configured to extract a first vascular territory corresponding to a fundus oculi vessel from the two-dimensional images formed by the first image forming part and extract a second vascular territory corresponding to the fundus oculi vessel from the accumulated images generated by the accumulated image forming part; and a specification part configured to specify the position of a vascular cross sectional region corresponding to a cross section of the fundus oculi vessel in the tomographic image based on the extracted first vascular territory and second vascular territory.

Still further, in the second aspect of the present invention, an opthalmologic image processing unit is connected to a first image forming part that forms a two-dimensional image of the surface of the fundus oculi of an eye and to a second image forming part that forms a tomographic image in a region of the surface of the fundus oculi corresponding to at least part of the two-dimensional image, and the opthalmologic image processing unit comprises: an accumulated image generating part configured to generate an accumulated image by accumulating the tomographic images formed by the second image forming part in the depth-wise direction; an extracting part configured to extract a first vascular territory corresponding to a fundus oculi vessel from the two-dimensional image formed by the first image forming part, and extract a second vascular territory corresponding to a fundus oculi vessel from the accumulated image generated by the accumulated image generating part; and a specification part configured to specify the position of a vascular cross sectional region corresponding to a cross section of a fundus oculi vessel in the tomographic image based on the extracted first vascular territory and second vascular territory.

Still further, in the third aspect of the present invention, an opthalmologic image processing program is characterized in that a computer connected to a first image forming part that forms a two-dimensional image of the surface of the fundus oculi of an eye and to a second image forming part that forms a tomographic image in a region of the surface of the fundus oculi corresponding to at least part of the two-dimensional image is made to: function as an accumulated image generating part that generates an accumulated image by accumulating the tomographic images formed by the second image forming part in the depth-wise direction; function as an extracting part that extracts a first vascular territory corresponding to a fundus oculi vessel from the two-dimensional image formed by the first image forming part and extracts a second vascular territory corresponding to a fundus oculi vessel from the accumulated image generated by the accumulated image generating part; and function as a specification part that specifies the position of a vascular cross sectional region corresponding to a cross section of the fundus oculi vessel in the tomographic image based on the extracted first vascular territory and second vascular territory.

BRIEF DESCRIPTION OF THE DRAWINGS

FIG. 8 is a schematic diagram representing one example of scanning features of signal light in a preferred embodiment of the fundus observation device related to the present invention.

DETAILED DESCRIPTION OF THE REFERENCE EMBODIMENTS

Figure 20:
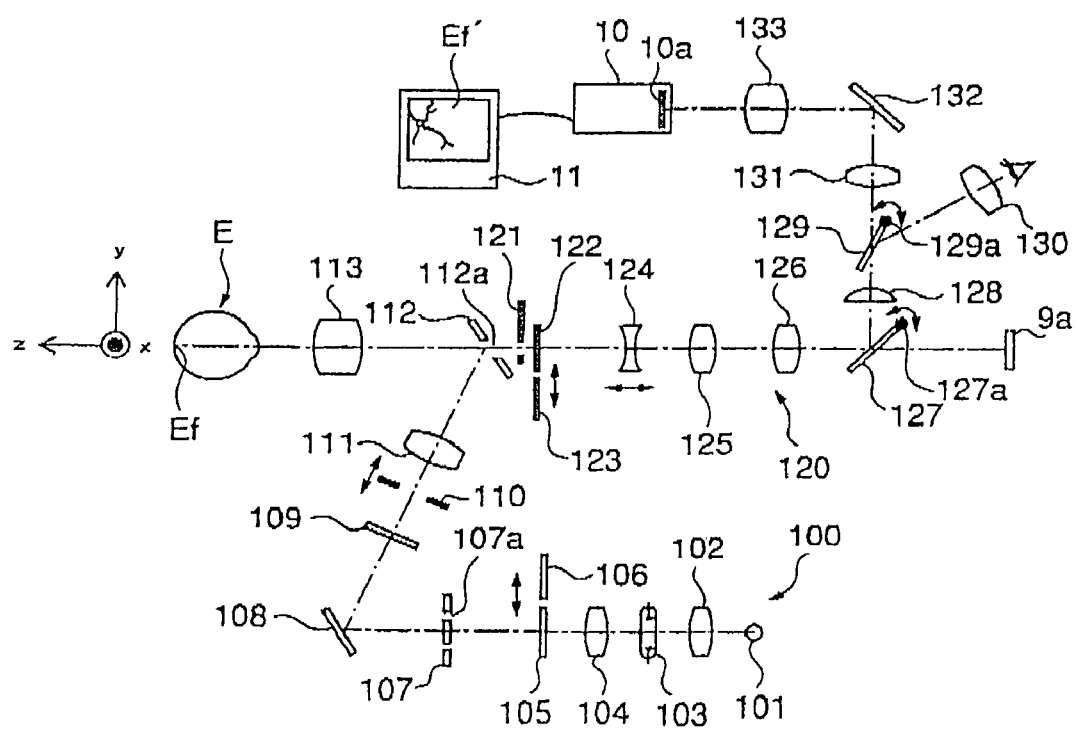
FIG. 20 is a schematic diagram representing one example of an internal constitution (an optical system constitution) of a conventional fundus observation device (fundus camera).
Figure 21:
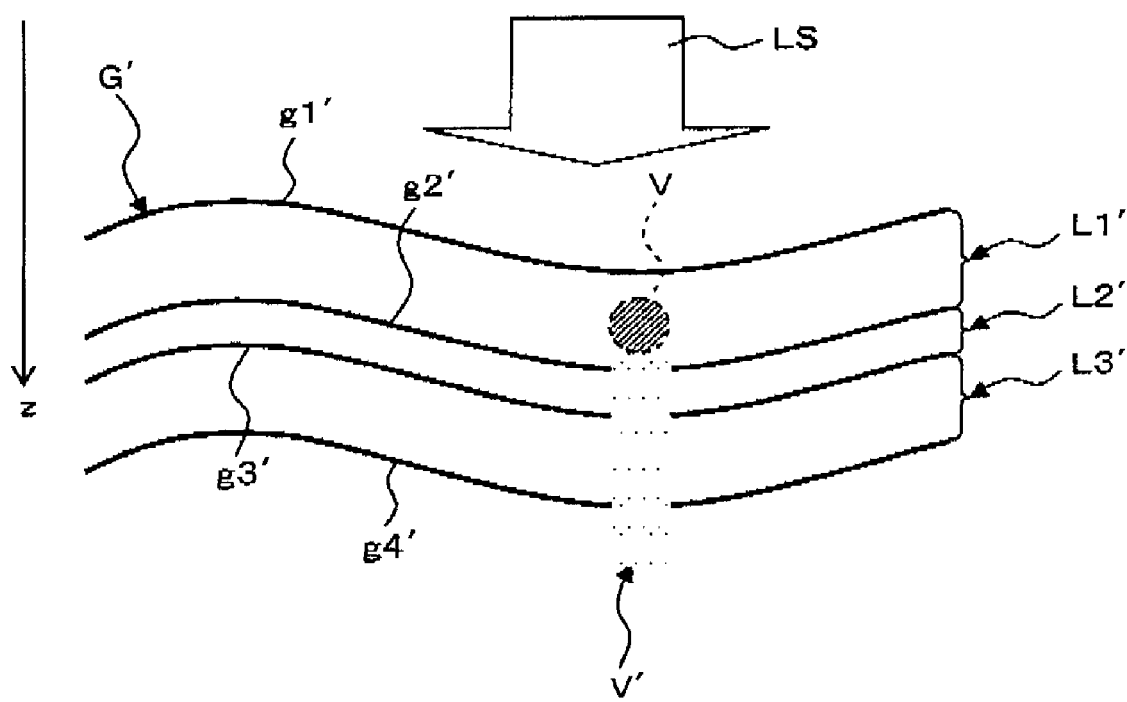
FIG. 21 is a schematic explanation view for explaining an example of image region located directly under the fundus oculi vessel in an OCT image.

Favorable embodiments of a fundus observation device, an opthalmologic image processing unit, an opthalmologic image processing program, and an opthalmologic image processing method according to the present invention are described in detail referring to figures. For structural parts that are the same as conventional ones, the same symbols used in FIG. 20 and FIG. 21 are used.

Figure 1:
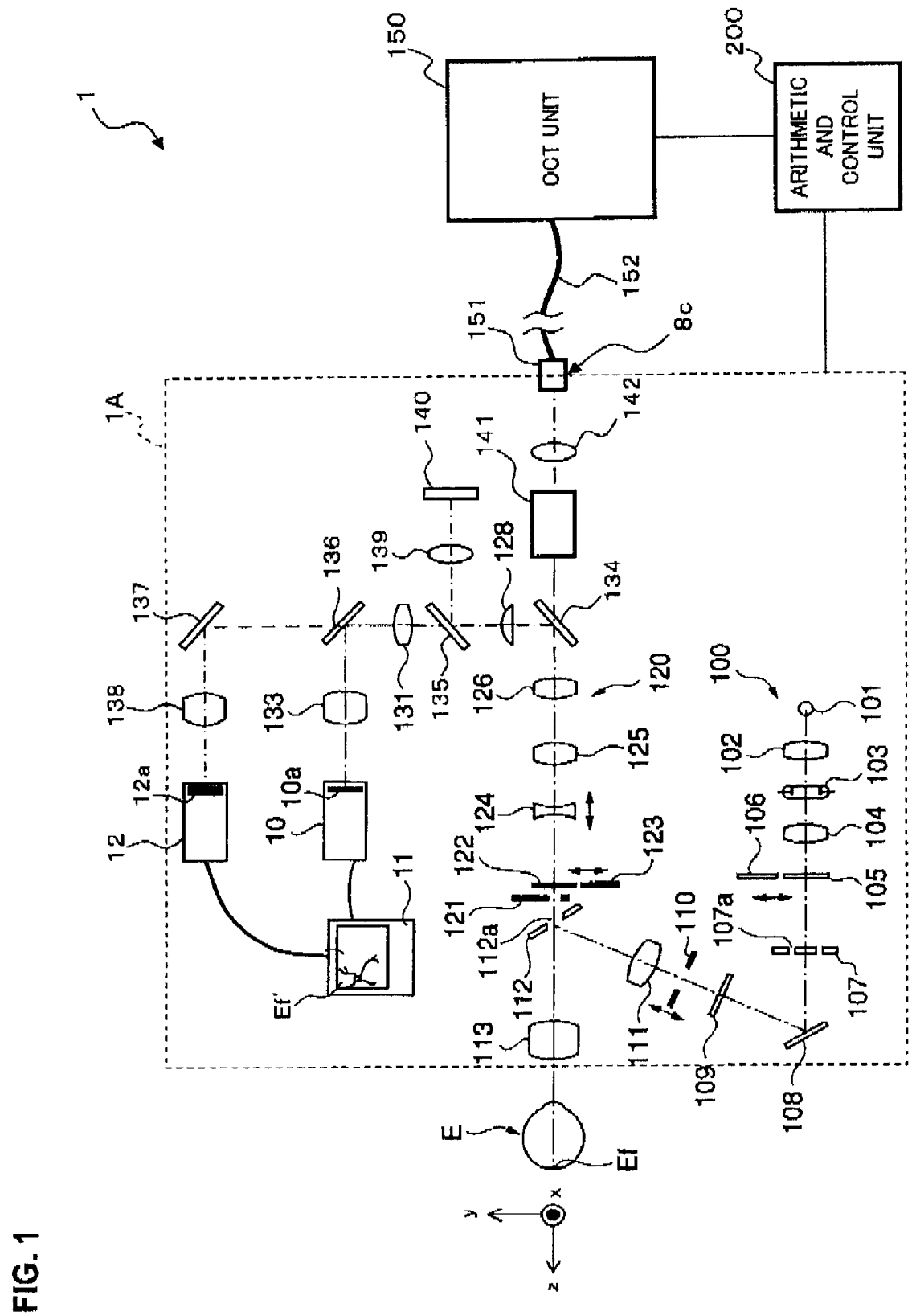
FIG. 1 is a schematic diagram representing one example of the entire constitution in a preferred embodiment of the fundus observation device related to the present invention.
Figure 2:
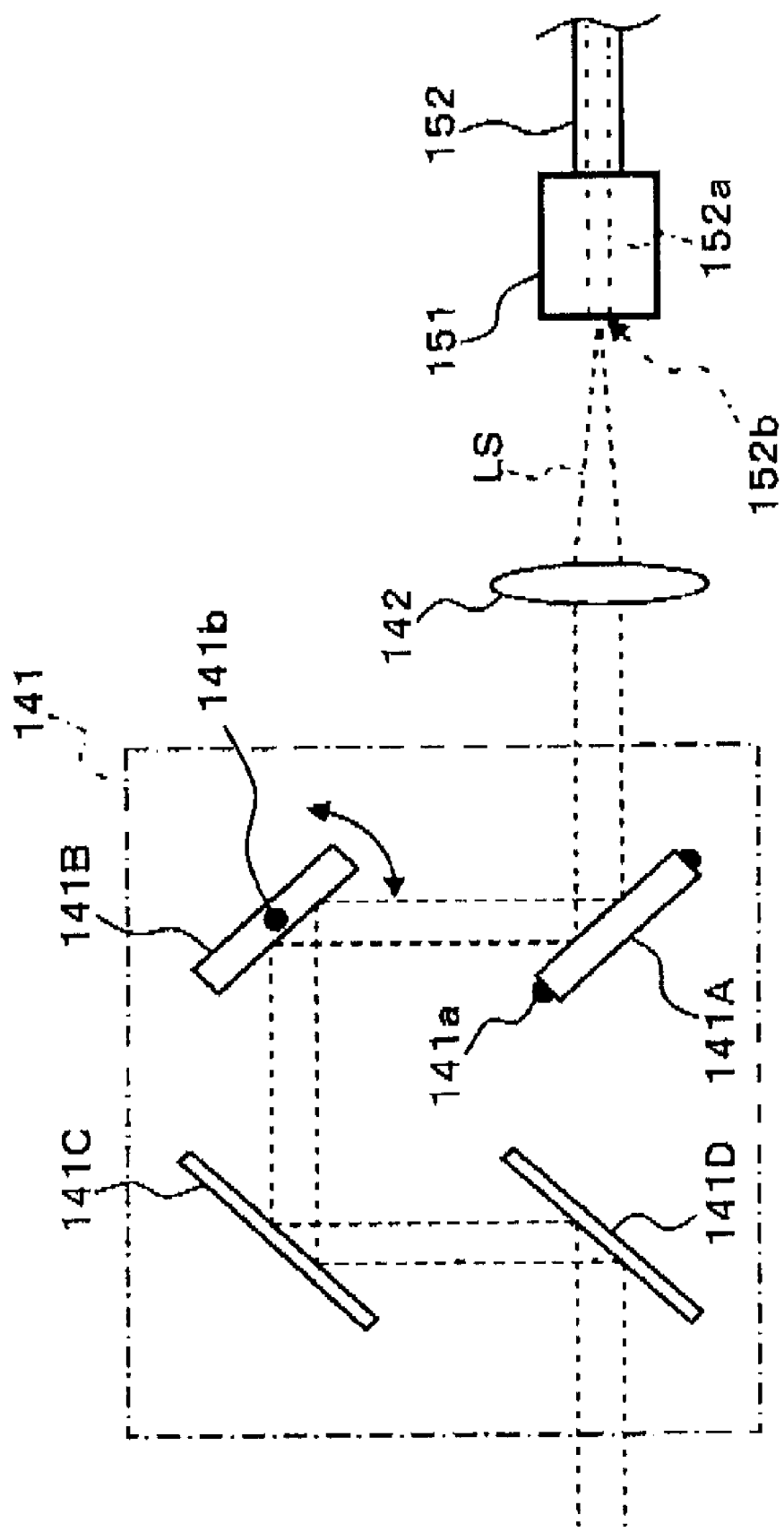
FIG. 2 is a schematic diagram representing one example of the constitution of a scanning unit installed in a fundus camera unit in a preferred embodiment of the fundus observation device related to the present invention.
Figure 3:
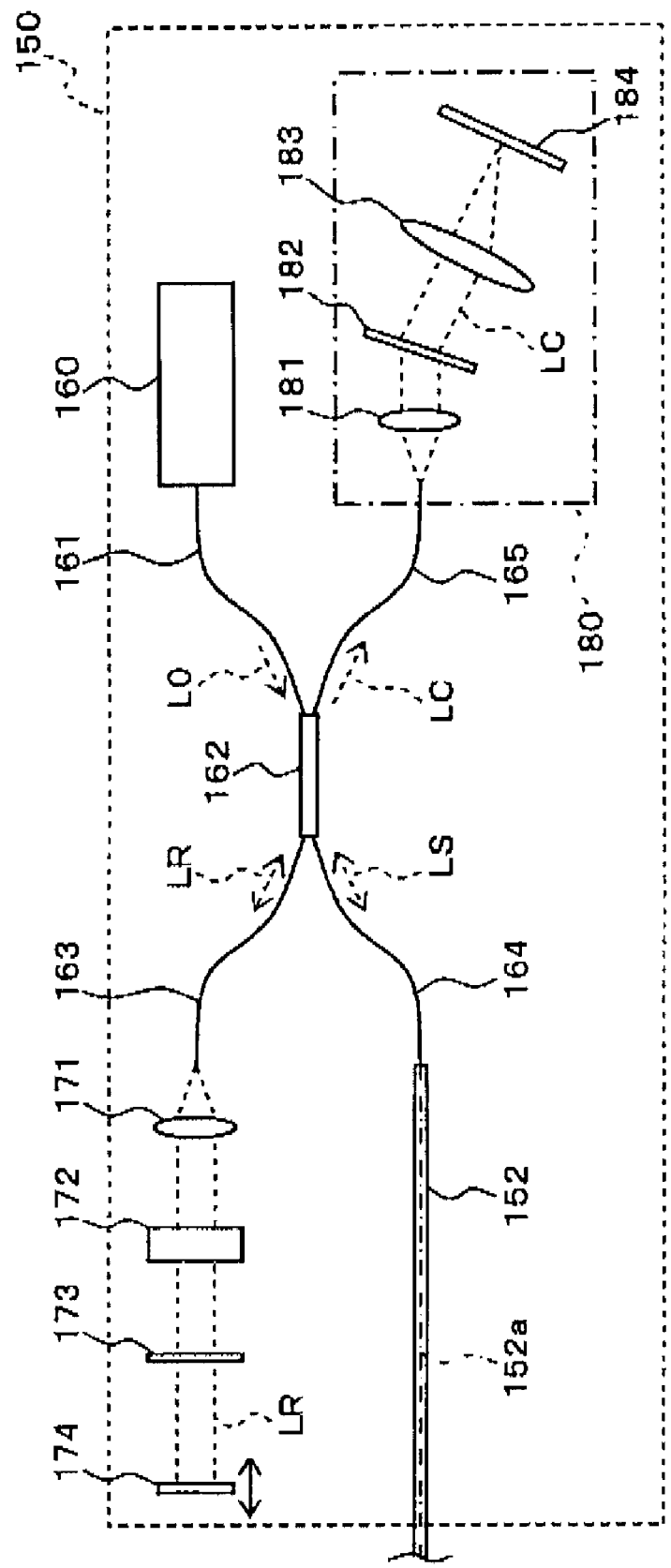
FIG. 3 is a schematic diagram representing one example of the constitution of an OCT unit in a preferred embodiment of the fundus observation device related to the present invention.
Figure 4:
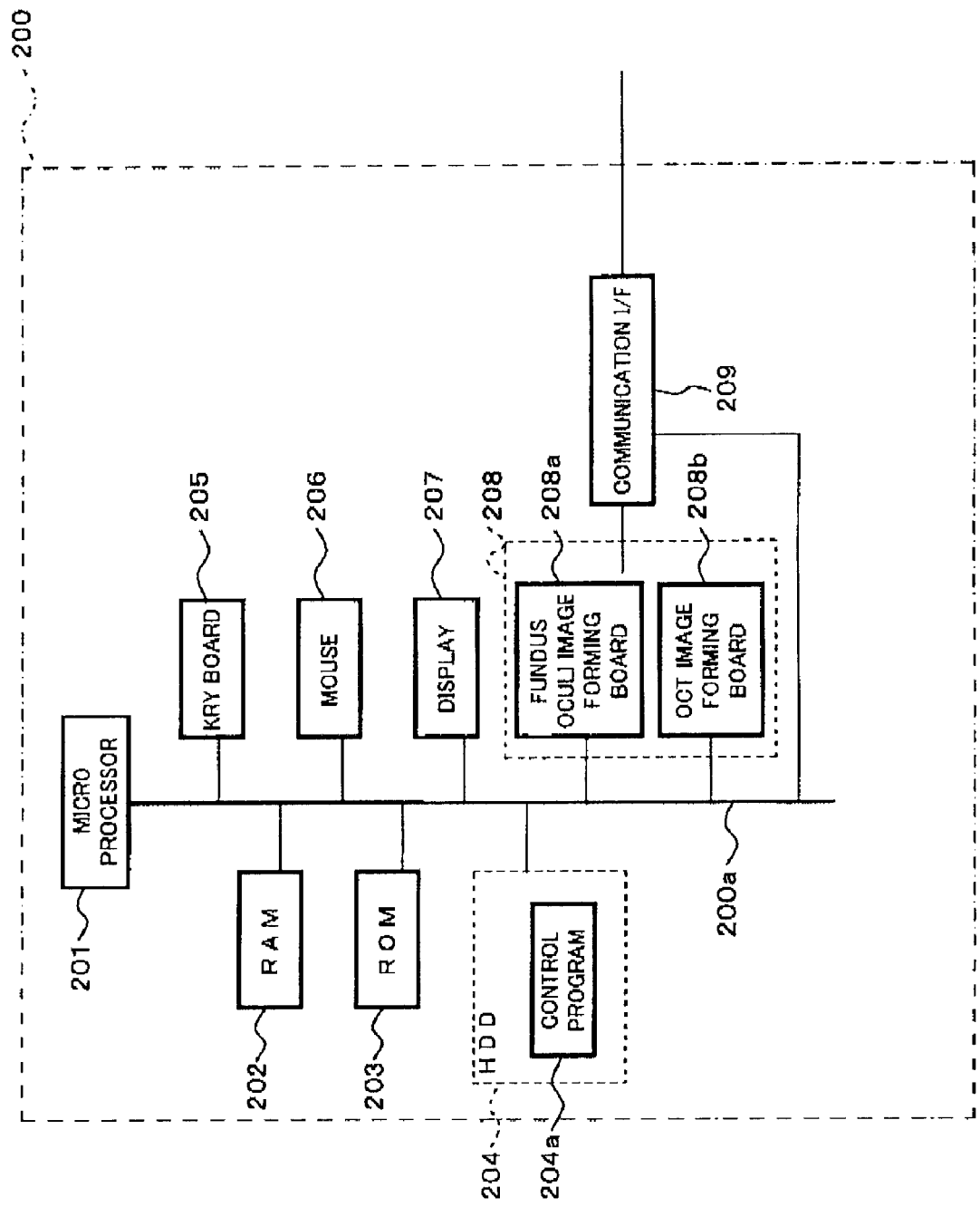
FIG. 4 is a schematic block diagram representing one example of hardware configurations of an arithmetic and control unit in an embodiment of the fundus observation device related to the present invention.
Figure 5:
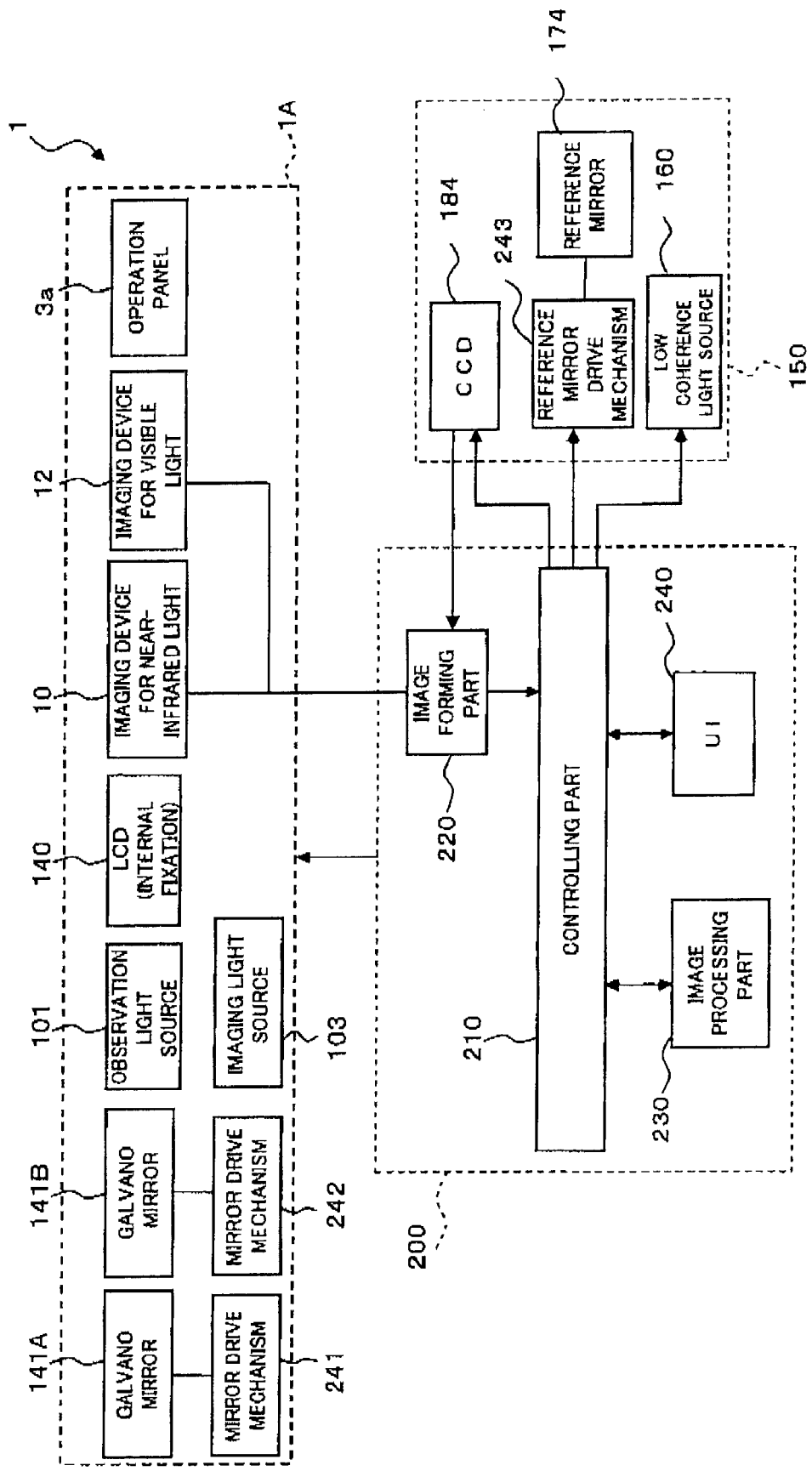
FIG. 5 is a schematic block diagram representing one example of the constitution of a control system in a preferred embodiment of the fundus observation device related to the present invention.
Figure 6:
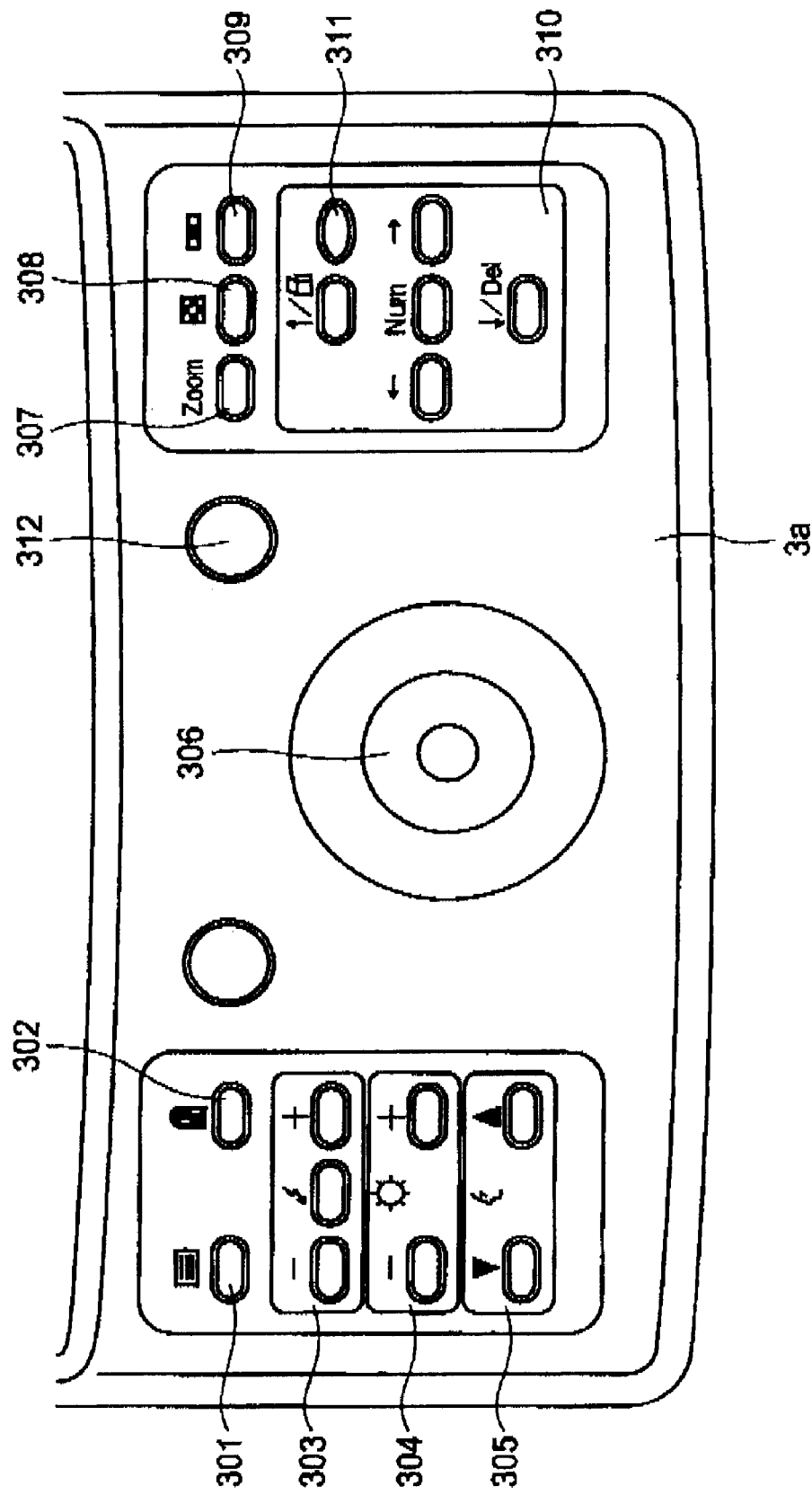
FIG. 6 is a schematic diagram showing an example of the appearance configuration of the operation panel in a preferred embodiment of the fundus observation device related to the present invention.
Figure 7:
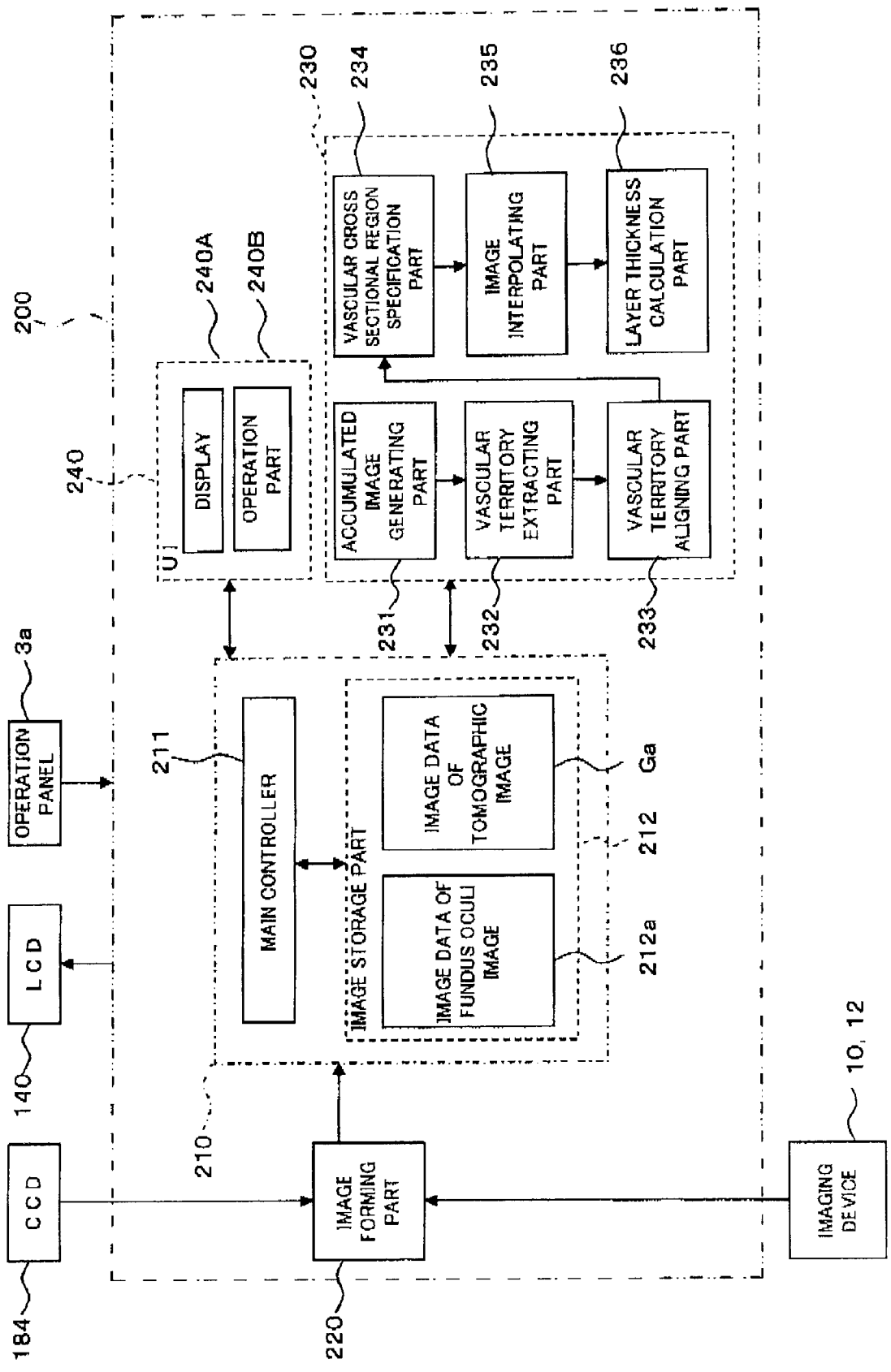
FIG. 7 is a schematic block diagram showing an example of a functional constitution of the arithmetic and control unit in a preferred embodiment of the fundus observation device related to the present invention.

First, by referring to FIGS. 1 through 7, the constitution of the fundus observation device related to the present invention is described. FIG. 1 shows an example of the entire constitution of a fundus observation device 1 related to the present invention. FIG. 2 shows an example of the constitution of a scanning unit 141 in a fundus camera unit 1A. FIG. 3 shows an example of the constitution of an OCT unit 150. FIG. 4 shows an example of the hardware configuration of an arithmetic and control unit 200. FIG. 5 shows an example of the configuration of a control system of the fundus observation device 1. FIG. 6 shows an example of the constitution of an operation panel 3*a* disposed to the fundus camera unit 1A. FIG. 7 shows an example of the configuration of a control system of the arithmetic and control unit 200.

The Entire Configuration

As shown in FIG. 1, the fundus observation device 1 comprises the fundus camera unit 1A that functions as a fundus camera, the OCT unit 150 accommodating the optical system of an optical image measuring device (OCT device), and the arithmetic and control unit 200 that executes various arithmetic processes and control processes, etc.

To the OCT unit 150, one end of a connection line 152 is attached. To the other end of this connection line 152, a connector part 151 is attached. This connector part 151 is mounted onto a mounting part 8*c* shown in FIG. 19. Further, a conductive optical fiber runs through the inside of the connection line 152. The OCT unit 150 and the fundus camera unit 1A are optically connected through the connection line 152. The constitution details of the OCT unit 150 are to be described later referring to FIG. 3.

Configuration of Fundus Camera Unit

The fundus camera unit 1A is a device configured for forming a two-dimensional image of the surface of a fundus oculi of an eye based on optically captured data (data detected by imaging devices 10 and 12). The fundus camera unit 1A has substantially the same appearance as the conventional fundus camera 1000 shown in FIG. 19. Furthermore, as in the conventional optical system shown in FIG. 20, the fundus camera unit 1A is provided with an illuminating optical system 100 to light a fundus oculi Ef of an eye E, and an imaging optical system 120 for guiding the illumination light reflected by the fundus oculi to an imaging device 10.

Although the details are to be described later, the imaging device 10 in the imaging optical system 120 of the present embodiment is used for detecting the illumination light having a wavelength in the near-infrared region. Further, in this imaging optical system 120, the imaging device 12 for detecting the illumination light having a wavelength in the visible region is provided separately. Furthermore, this imaging optical system 120 guides the signal light from the OCT unit 150 to the fundus oculi Ef, and also guides the signal light passed through the fundus oculi Ef to the OCT unit 150.

Like the conventional ones, the illuminating optical system 100 comprises: an observation light source 101, a condenser lens 102, an imaging light source 103, a condenser lens 104, exciter filters 105 and 106, a ring transparent plate 107, a mirror 108, an LCD 109, an illumination diaphragm 110, a relay lens 111, an aperture mirror 112, and an objective lens 113.

The observation light source 101 emits the illumination light having a wavelength in the visible region included within, for example, about 400 nm to 700 nm. Further, the imaging light source 103 emits the illumination light having a wavelength in the near-infrared region included within, for example, about 700 nm to 800 nm. The near-infrared light emitted from this imaging light source 103 is provided shorter than the wavelength of the light used by the OCT unit 150 (to be described later).

The imaging optical system 120 comprises: the objective lens 113, the aperture mirror 112 (aperture part 112*a* thereof), an imaging diaphragm 121, barrier filters 122 and 123, a variable magnifying lens 124, a relay lens 125, an imaging lens 126, a dichroic mirror 134, a field lens 128, a half mirror 135, a relay lens 131, a dichroic mirror 136, an imaging lens 133, the imaging device 10 (an image pick-up element 10*a*), a reflection mirror 137, an imaging lens 138, the imaging device 12 (an image pick-up element 12*a*), a lens 139, and an LCD (Liquid crystal Display) 140.

The imaging optical system 120 related to the present embodiment is different from the conventional imaging optical system 120 shown in FIG. 20 in that the dichroic mirror 134, the half mirror 135, the dichroic mirror 136, the reflection mirror 137, the imaging lens 138, the lens 139 and the LCD 140 are provided.

The dichroic mirror 134 reflects the fundus reflection light (having a wavelength included within about 400 nm to 800 nm) of the illumination light from the illuminating optical system 100, and transmits the signal light LS (having a wavelength included within, for example, about 800 nm to 900 nm; to be described later) from the OCT unit 150.

The dichroic mirror 136 transmits the illumination light having a wavelength in the visible region from the illuminating optical system 100 (the visible light of a wavelength within about 400 nm to 700 nm emitted from the observation light source 101), and reflects the illumination lights having a wavelength in the near-infrared region (near-infrared light of a wavelength within about 400 nm to 700 nm emitted from the observation light source 103).

The LCD 140 shows an internal fixation target, etc. The light from this LCD 140 is converged by the lens 139, and thereafter reflected by the half mirror 135 to the dichroic mirror 134 via the field lens 128. Then, it enters the eye E after passing through the imaging lens 126, the relay lens 125, the variable magnifying lens 124, the aperture mirror 112 (aperture part 112*a* thereof), the objective lens 113, etc. As a result, an internal fixation target, etc. is displayed in the fundus oculi Ef of the eye E.

The image pick up element 10*a* is an image pick up element such as CCD and CMOS installed internally in the imaging device 10 such as a TV camera, and is particularly used for detecting light of a wavelength in the near-infrared region (that is, the imaging device 10 is an infrared TV camera for detecting near-infrared light). The imaging device 10 outputs the video signal as a result of detection of near-infrared light. A touch panel monitor 11 displays a two-dimensional image of the surface of the fundus oculi Ef (a fundus image Ef') based on this video signal. This video signal is sent to the arithmetic and control unit 200, and the fundus oculi image is displayed on the display (to be described later). When the fundus oculi are being imaged by this imaging device 10, for example, the illumination light emitted from the imaging light source 103 of the illuminating optical system 100, having a wavelength in the near-infrared region, may be used.

Also, the image pick up element 12*a* is an image pick up element such as CCD and CMOS installed internally in the imaging device 12 such as a TV camera, and is particularly used for detecting light of a wavelength in the visible region (that is, the imaging device 12 is a TV camera for detecting visible light). The imaging device 12 outputs the video signal as a result of detection of visible light. The touch panel monitor 11 displays a two-dimensional image (fundus image Ef') of the surface of the fundus oculi Ef based on this video signal. This video signal is sent to the arithmetic and control unit 200, and the fundus oculi image is displayed on the display (to be described later). When the fundus oculi are being imaged by this imaging device 12, for example, the illumination light emitted from the observation light source 101 of the illuminating optical system 100, having a wavelength in the visible region, may be used.

The imaging optical system 120 of the present embodiment is provided with a scanning unit 141 and a lens 142. The scanning unit 141 is equipped with a constitution to scan the light (signal light LS; to be described later) emitted from the OCT unit 150 on the fundus oculi Ef, and functions as an example of "a scanning part" of the present invention.

The lens 142 makes the signal light LS guided through the connection line 152 from the OCT unit 150 enter the scanning unit 141 in the form of parallel light flux. Further, the lens 142 acts so as to converge the fundus reflection light of the signal light LS that has reached through the scanning unit 141.

In FIG. 2, one example of a concrete constitution of the scanning unit 141 is shown. The scanning unit 141 comprises Galvano mirrors 141A, 141B, and reflection mirrors 141C, 141D.

The Galvano mirrors 141A and 141B are to be rotatable around rotary shafts 141a and 141b respectively. The rotary shafts 141a and 141b are arranged perpendicular to each other. In FIG. 2, the rotary shaft 141a of the Galvano mirror 141A is arranged parallel to the paper face, while the rotary shaft 141b of the Galvano mirror 141B is arranged perpendicular to the paper face. That is, the Galvano mirror 141B is to be rotatable in the directions indicated by an arrow pointing in both directions in FIG. 2, while the Galvano mirror 141A is to be rotatable in the directions perpendicular to the arrow pointing in both directions. As a result, this pair of Galvano mirrors 141A and 141B act so that the reflecting direction of the signal light LS changes to a direction perpendicular to each other. The rotary movement of the respective Galvano mirrors 141A and 141B is driven by a mirror drive mechanism (see FIG. 5) to be described later.

The signal light LS reflected by the Galvano mirrors 141A and 141B is to be reflected by reflection mirrors 141C and 141D, and is to advance in the same direction as having entered into the Galvano mirror 141A.

As described before, a conductive optical fiber 152a runs inside the connection line 152, and an end face 152b of the optical fiber 152a is arranged so as to face the lens 142. The signal light LS emitted from this end face 152b advances toward the lens 142 while gradually expanding its beam diameter until being converged to a parallel light flux by this lens 142. On the contrary, the fundus reflection light of the signal light LS is converged toward the end face 152b by this lens 142.

Configuration of OCT Unit

Next, the configuration of the OCT unit 150 is described with reference to FIG. 3. The OCT unit 150 shown in the FIG. 3 is a device for forming a tomographic image of fundus oculi based on data captured by optical scan (data detected by CCD 184 to be described below). The OCT unit 150 has a similar optical system to that of a conventional optical image measuring device. That is, the OCT unit 150 has an interferometer that splits the light emitted from a light source into a reference light and a signal light and generates interference light by superposing the reference light having reached the reference object and the signal light having reached the object to be measured (fundus oculi Ef), and a part configured to output a signal as a result of detection of the interference light toward the arithmetic and control unit 200. The arithmetic and control unit 200 forms an image of the object to be measured (fundus oculi Ef) by analyzing this signal.

A low coherence light source 160 is composed of a broad band light source such as super luminescent diode (SLD) or a light emitting diode (LED) that emits low coherence light L0. This low coherence light L0, for instance, has a wavelength in the near-infrared region and is supposed to be light having a time-wise coherence length of approximately several tens of micrometers. The low coherence light L0 emitted from the low coherence light source 160 has a longer wavelength than the illumination light (wavelength: about 400 nm to 800 nm) of the fundus camera unit 1A, for example, a wavelength included within about 800 nm to 900 nm. This low coherence light source 160 corresponds to an example of the "light source" of the present invention.

The low coherence light L0 emitted from the low coherence light source 160 is guided to an optical coupler 162 through an optical fiber 161 composed of, e.g. a single mode fiber, or PM (Polarization maintaining) fiber. The optical coupler 162 splits the low coherence light L0 into reference light LR and signal light LS.

The optical coupler 162 has both functions of a device for splitting lights (splitter), and a device for superposing lights (coupler); however, herein conventionally referred to as an "optical coupler".

The reference light LR generated by the optical coupler 162 is guided by an optical fiber 163 composed of a single mode fiber and the like, and emitted from the end face of the fiber. The emitted reference light LR is converged into a parallel light flux by a collimator lens 171, and thereafter, passed through a glass block 172 and a density filter 173, and then reflected by a reference mirror 174 (reference object).

The reference light LR reflected by the reference mirror 174 is passed through the density filter 173 and the glass block 172 again and then converged to the end face of the optical fiber 163 by the collimator lens 171. The converged reference light LR is guided to the optical coupler 162 through the optical fiber 163.

The glass block 172 and the density filter 173 act as a delaying part for matching the optical path length (optical distance) of the reference light LR and the signal light LS, and also as a part for matching the dispersion characteristics of reference light LR and the signal light LS.

Further, the reference mirror 174 is provided to be movable in the propagating direction of the reference light LR (arrow direction shown in FIG. 3). As a result, it ensures the light path length of the reference light LR according to the axial length, etc. of the eye E. The reference mirror 174 is operated to move by a drive mechanism including a drive device such as a motor (a reference mirror drive mechanism 243 described later; refer to FIG. 5).

Whereas, the signal light LS generated by the optical coupler 162 is guided to the end part of the connection line 152 by an optical fiber 164 composed of a single mode fiber and the like. The conductive optical fiber 152a runs inside the connection line 152. Herein, the optical fiber 164 and the optical fiber 152a may be composed of a single optical fiber, or may be jointly formed by connecting ends of the respective fibers. In either case, it is sufficient as long as the optical fibers 164 and 152a are composed so as to be capable of transferring the signal light LS between the fundus camera unit 1A and the OCT unit 150.

The signal light LS is guided within the connection line 152 to the fundus camera unit 1A. Then, the signal light LS enters into the eye E through the lens 142, the scanning unit 141, the dichroic mirror 134, the imaging lens 126, the relay lens 125, the variable magnifying lens 124, the imaging diaphragm 121, the aperture part 112a of the aperture mirror 112, and the objective lens 113 (at this moment, the barrier filters 122 and 123 are retracted from the optical path respectively).

The signal light LS that has entered into the eye E forms an image on the fundus oculi (retina) Ef and is then reflected. At this moment, the signal light LS is not only reflected on the surface of the fundus oculi Ef, but also scattered at the refractive index boundary reaching the deep area of the fundus oculi Ef. As a result, the signal light LS reached the fundus Ef becomes a light containing the information reflecting the surface state of the fundus oculi Ef and the information reflecting the scattered state in the rear at the refractive index boundary of the deep area tissue of the fundus oculi. The light may simply be referred to as "fundus reflection light of the signal light LS.

The fundus reflection light of the signal light LS advances reversely on the above path and converges at the end face 152b of the optical fiber 152a, then enters into the OCT unit 150 through this optical fiber 152a, and returns to the optical coupler 162 through the optical fiber 164. The optical coupler 162 overlays this signal light LS on the reference light LR reflected at the reference mirror 174 to generate interference light LC. The generated interference light LC is guided into a spectrometer 180 through an optical fiber 165 composed of a single mode fiber and the like.

Herein, the "interference light generation part" in the present invention is composed of an interferometer including at least the optical coupler 162, the optical fibers 163 and 164, and the reference mirror 174. Although a Michelson type interferometer is adopted in the present embodiment, for instance, a Mach Zender type, etc. or any optional type of interferometer may be adopted appropriately.

The spectrometer 180 comprises a collimator lens 181, a diffraction grating 182, an image forming lens 183, and a CCD (Charge Coupled Device) 184. The diffraction grating 182 in the present embodiment is a transmission type diffraction grating; however, needless to say, a reflection type diffraction grating may also be used. Further, needless to say, in place of the CCD 184, it is also possible to adopt other photo-detecting elements. This photo-detecting element is one example of the "detecting part" in the present invention.

The interference light LC entered the spectrometer 180 is to be resolved into spectra by the diffraction grating 182 after having been converged into a parallel light flux by the collimator lens. The split interference light LC forms an image on the image pick up surface of the CCD 184 by the image forming lens 183. The CCD 184 receives this interference light LC to convert into an electrical detection signal, and outputs this detection signal to the arithmetic and control unit 200.

Configuration of Arithmetic and Control Unit

Next, the configuration of the arithmetic and control unit 200 is described. The arithmetic and control unit 200 functions as one example of the "opthalmologic image processing unit" in the present invention.

This arithmetic and control unit 200 analyzes the detection signal input from the CCD 184 of the spectrometer 180 of the OCT unit 150, and performs a process of forming tomographic images of the fundus oculi Ef of the eye E. The analysis technique then is the same technique as the conventional Fourier domain OCT technique.

Further, the arithmetic and control unit 200 performs a process of forming (image data of) a two-dimensional image showing the state of the surface of the fundus oculi Ef (retina) based on the video signal output from the imaging devices 10 and 12 of the fundus camera unit 1A.

Furthermore, the arithmetic and control unit 200 executes the control of each part of the fundus camera unit 1A and the control of each part of the OCT unit 150.

As for the control of the fundus camera unit 1A, to be controlled is, for example: the emission of illumination light by the observation light source 101 or the imaging light source 103; the insertion/retraction operation of the exciter filters 105, 106, or the barrier filters 122, 123 on the optical path; the display operation of the liquid crystal display 140, etc.; the shift of the illumination diaphragm 110 (controlling the diaphragm value); the diaphragm value of the imaging diaphragm 121; the shift of the variable magnifying lens 124 (controlling the magnification), etc. Besides, the arithmetic and control unit 200 controls rotary operations of the Galvano mirrors 141A and 141B of the scanning unit 141.

Whereas, as for the control of the OCT unit 150, control of the emission of the low coherence light by the low coherence light source 160, control of the shift of the reference mirror 174, control of the accumulation time of the CCD 184, etc. are performed.

One example of the hardware configuration of the arithmetic and control unit 200 that acts as described above is explained referring to FIG. 4. The arithmetic and control unit 200 is provided with the same hardware configuration as conventional computers. To be specific, the configuration includes: a microprocessor 201 (CPU, MPU, etc.), a RAM202, a ROM203, a hard disk drive (HDD) 204, a keyboard 205, a mouse 206, a display 207, an image forming board 208, and a communication interface (I/F) 209. These parts are connected through a bus 200a.

The microprocessor 201 executes operations characteristic to the present embodiment by loading a control program 204a that has been stored in the hard disk drive 204, on the RAM 202. This control program 204a is one example of the "opthalmologic image processing program" in the present invention.

Further, the microprocessor 201 executes control of each part of the device described above, various arithmetic processes, etc. Furthermore, control of each part of the device in response to an operation signal from the keyboard 205 or the mouse 206, control of display processes by the display 207, and control of transmitting/receiving processes of various types of data, control signals, etc. are executed by the communication interface 209.

The keyboard 205, the mouse 206 and the display 207 are used as a user interface of the fundus observation device 1. The keyboard 205 is used as a device for inputting letter, figures, etc. by typing. The mouse 206 is used as a device for performing various input operations to the display screen of the display 207.

Further, the display 207, which is an arbitrary display device such as LCD (Liquid Crystal Display) or CRT (Cathode Ray Tube), displays images of the fundus oculi Ef formed by the fundus observation device 1 and displays various operation screens, set-up screens, etc.

The user interface of the fundus observation device 1 is not limited to such a configuration but may be configured by using any user interfaces equipped with a function to display various information and a function to input various information, such as track ball, control lever, touch panel type LCD, control panel for opthalmology examinations.

An image forming board 208 is an electronic circuit dedicated for operating to form (image data of) the image of the fundus oculi Ef of the eye E. In this image forming board 208, a fundus image forming board 208a and an OCT image forming board 208b are installed. The fundus image forming board 208a is an electronic circuit dedicated for operating in order to form image data of an image of the fundus oculi based on the video signal from the imaging device 10 or the imaging device 12 of the fundus camera unit 1A. Further, the OCT image forming board 208b is an electronic circuit dedicated for operating in order to form image data of tomographic images of the fundus oculi Ef based on the detecting signal from the CCD 184 of the spectrometer 180 in the OCT unit 150. Installation of the image forming board 208 may increase the processing speed for forming image data of fundus images and tomographic images.

A communication interface 209 operates to send the control signal from the microprocessor 201 to the fundus camera unit 1A and the OCT unit 150. Also, the communication interface 209 operates to receive the video signal from the imaging devices 10 and 12 in the fundus camera unit 1A and the detecting signal from the CCD 184 in the OCT unit 150 and input the signals to the image forming board 208. At this time, the communication interface 209 operates to input the video signal from the imaging devices 10 and 12 to the fundus image forming board 208a, and operates to input the detecting signal from the CCD 184 to the OCT image forming board 208b.

Moreover, when the arithmetic and control unit 200 is connected to a network such as LAN (Local Area Network) or Internet, etc., the communication interface 209 may be configured to be equipped with a network adopter such as a LAN card or communication equipment such as a modem so as to be able to perform data communication through the network. In this case, a server accommodating the control program 204a may be installed on the network, and at the same time, the arithmetic and control unit 200 may be configured as a client terminal of the server.

Control System Configuration

The configuration of the control system of the fundus observation device 1 having the configuration described above is explained referring to FIGS. 5 to 7. FIG. 5 is a block diagram showing a part relating to the operations and processes in the present embodiment, which has been particularly selected from among constituents composing the fundus observation device 1. FIG. 6 shows one example of the constitution of an operation panel 3a provided on the fundus camera unit 1A. FIG. 7 is a block diagram showing a detailed constitution of the arithmetic and control unit 200.

Controlling Part

The control system of the fundus observation device 1 is configured mainly having a controlling part 210 of the arithmetic and control unit 200. The controlling part 210 includes the microprocessor 201, the RAM 202, the ROM 203, the hard disk drive 204 (control program 204a), and the communication interface 209.

The controlling part 210 executes the aforementioned control processes by the microprocessor 201 that is operated based on the control program 204a. In particular, the controlling part 210 executes control of the mirror drive mechanisms 241 and 242 of the fundus camera unit 1A to make the Galvano mirrors 141A and 141B work independently as well as control of the reference mirror drive mechanism 243 to move the reference mirror 174 toward the direction in which the reference light LR travels.

Furthermore, the controlling part 210 executes control for causing the display 207 of the user interface 240 to display two kinds of images produced by the fundus observation device 1: that is, a two-dimensional image (fundus image Ef′) of the surface of the fundus oculi Ef by the fundus camera unit 1A, and a tomographic image of the fundus oculi Ef formed based on the detection signal obtained by the OCT unit 150. These images can be displayed on the display 207 both respectively and simultaneously. The details of the constitution of the controlling part 210 will be described later referring to FIG. 7.

Image Forming Part

An image forming part 220 operates a process of forming image data of the fundus image based on the video signal from the imaging devices 10 and 12 of the fundus camera unit 1A, and a process of forming image data of the tomographic images of the fundus oculi Ef based on the detecting signal from the CCD 184 in the OCT unit 150. This imaging forming part 220 comprises the imaging forming board 208 and the communication interface 209. "Image" may be identified with "image data" corresponding thereto in the specification.

Herein, each part of the fundus camera unit 1A for capturing a two-dimensional image of the surface of the fundus oculi Ef and the image forming part 220 are explained as one example of the "first image forming part" in the present invention. Further, each part of the fundus camera unit 1A for capturing a tomographic image of the fundus oculi Ef, the OCT unit 150, and the image forming part 220 (OCT image forming board 208b) are explained as one example of the "second image forming part" in the present invention.

Image Processing Part

An image processing part 230 is used for various image processes to image data of the images formed by the image forming part 220. For example, the image processing part 130 operates to form image data of a three-dimensional image of the fundus oculi Ef based on the tomographic images of the fundus oculi Ef corresponding to the detection signal from the OCT unit 150, and executes various corrections, such as adjustment of brightness of the images.

Further, the image processing part 230, as is conventionally done, executes processes to extract an image region corresponding to the various layers (e.g. retina) included in tomographic images of the fundus oculi Ef (a layer region described later) and an image region corresponding to the boundary between layers (a boundary region described later). Furthermore, the image processing part 230 executes processes described later, in connection with the details of the present embodiment (see FIG. 7).

Image data of a three-dimensional image is image data made by assigning a pixel value to each of a plurality of voxels arranged three-dimensionally, and is referred to as volume data, voxel data, and so forth. In the case of display of an image based on volume data, the image processing part 230 operates to form image data of a pseudo three-dimensional image seen from a specified viewing direction by applying a rendering process (such as volume rendering and MIP (Maximum Intensity Projection)) to the volume data. A display device such as the display device 207 will display such a pseudo three-dimensional image based on the image data.

The image processing part 230 comprises the microprocessor 201, RAM 202, ROM 203, and the hard disk drive 204 (control program 204a).

User Interface

The user interface (UI) 240, as shown in FIG. 7, comprises a display part 240A consisting of a display device such as the display 207, and an operation part 240B consisting of an operation device and an input device such as the keyboard 205 and mouse 206. The display part 240A functions as one example of "displaying part".

Operation Panel

Figure 19:
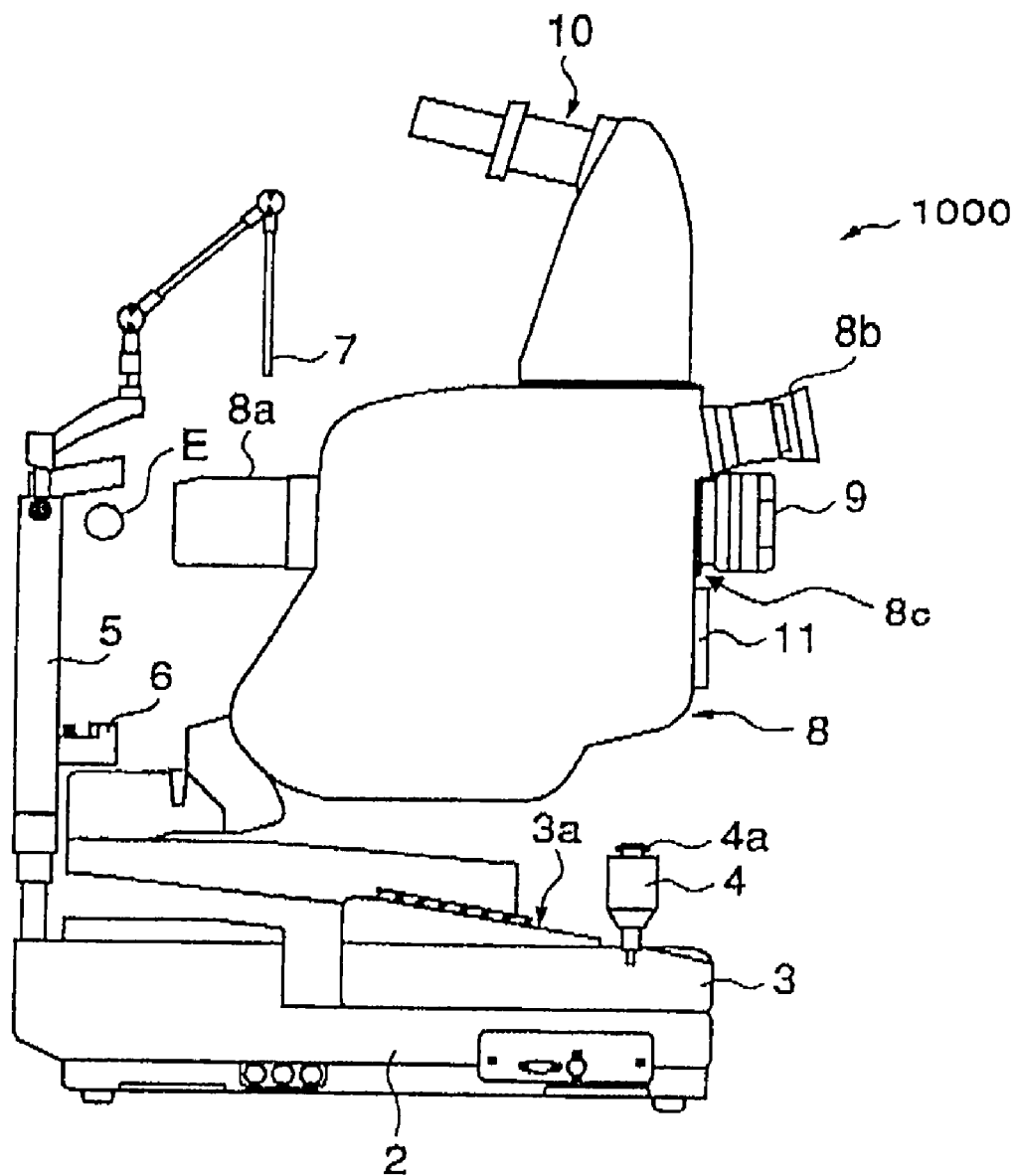
FIG. 19 is a schematic diagram showing one example of the appearance of a conventional fundus observation device (fundus camera).

The operation panel 3a of the fundus camera unit 1A will be described below. This operation panel 3a is arranged, for example, on the platform 3 of the fundus camera unit 1A as shown in FIG. 19. Different from the conventional configuration described above, the operation panel 3a in the present embodiment is provided with an operating part used to input an operation request for capturing a two-dimensional image of the surface of the fundus oculi Ef (the fundus oculi image Ef′) and an operating part used for an input operation for capturing a tomographic image of the fundus oculi Ef (traditionally, only the former operating part is provided). In this embodiment, by providing such control panel 3a, the operations for obtaining the fundus oculi image Ef′ and for obtaining the tomographic image can be performed with the same operation as the conventional fundus camera.

The operation panel 3a in the present embodiment is, as shown in FIG. 6, provided with a menu switch 301, a split switch 302, an imaging light amount switch 303, an observation light amount switch 304, a jaw holder switch 305, a photographing switch 306, a zoom switch 307, an image switching switch 308, a fixation target switching switch 309, a fixation target position adjusting switch 310, a fixation target size switching switch 311, and a mode switching knob 312.

The menu switch 301 is a switch operated to display a specified menu screen for a user to select and specify various types of menus (such as a photographing menu for photographing a two-dimensional image of the surface of the fundus oculi Ef and a tomographic image of the fundus oculi Ef, and a setting menu for inputting various types of settings). When this menu switch 301 is operated, the operation signal is input to the controlling part 210. The controlling part 210 displays a menu screen on the touch panel monitor 11 or the display part 240A in response to the input of this operation signal. Incidentally, a controlling part (not shown) may be provided in the fundus camera unit 1A and this controlling part may cause the touch panel monitor 11 to display the menu screen.

The split switch 302 is a switch operated to switch the light on and off of the split bright line for focusing (e.g., see JP Patent laid-open No. H9-66031 or the like. Also referred to as split target, split mark and so on.). Incidentally, the configuration for projecting this split bright line onto the eye E (split bright line projection part) is housed, for example, in the fundus camera unit 1A (omitted in FIG. 1). When the split switch 302 is operated, the operation signal is input to the controlling part 210 (or the above controlling part in the fundus camera unit 1A; hereinafter same as this). The controlling part 210 projects the split bright line onto the eye E by controlling the split bright line projection part in response to the input of this operation signal.

The imaging light amount switch 303 is a switch operated to adjust the emitted light amount of the imaging light source 103 (photographing light amount) depending on the state of the eye E (such as the degree of opacity of the lens). This imaging light amount switch 303 is provided with, for example, a photographing light amount increasing switch "+" for increasing the photographing light amount, a photographing light amount decreasing switch "−" for decreasing the photographing light amount, and a reset switch (button in the middle) for setting the photographing ling amount to a predetermined initial value (default value). When one of the imaging light amount switches 303 is operated, the operation signal is input to the controlling part 210. The controlling part 210 adjusts the photographing light amount by controlling the imaging light source 103 depending on the input operation signal.

The observation light amount switch 304 is a switch operated to adjust the emitted light amount (observation light amount) of the observation light source 101. The observation light amount switch 304 is provided with, for example, an observation light amount increasing switch "+" for increasing the observation light amount and an observation light amount decreasing switch "−" for decreasing the observation light amount. When one of the observation light amount switches 304 is operated, the operation signal is input to the controlling part 210. The controlling part 210 adjusts the observation light amount by controlling the observation light source 101 depending on the input operation signal.

The jaw holder switch 305 is a switch to move the position of the jaw holder 6 shown in FIG. 19. This jaw holder switch 305 is provided with, for example, an upward movement switch (upward triangle) for moving the jaw holder 6 upward and a downward movement switch (downward triangle) for moving the jaw holder 6 downward. When one of the jaw holder switches 305 is operated, the operation signal is input to the controlling part 210. The controlling part 210 moves the jaw holder 6 upward or downward by controlling a holder movement mechanism (not shown) depending on the input operation signal.

The photographing switch 306 is a switch used as a trigger switch for capturing a two-dimensional image of the surface of the fundus oculi Ef or a tomographic image of the fundus oculi Ef. When the photographing switch 306 is operated with a menu to photograph a two-dimensional image selected, the controlling part 210 having received the operation signal controls the imaging light source 103, and the display part 240A or the touch panel monitor 11. The imaging light source 103 is controlled to emit the photographing illumination light. The display part 240A or the touch panel monitor 11 is controlled to display a two-dimensional image of the surface of the fundus oculi Ef, based on the video signal output from the imaging device 10 that has detected the fundus reflection light. On the other hand, when the photographing switch 306 is operated while a menu to capture a tomographic image is selected, the controlling part 210 that has received the operation signal controls the low coherence light source 160, Galvano mirrors 141A and 141B, and display part 240A or the touch panel monitor 11. The low coherence light source 160 is controlled to emit the low coherence light L0. The Galvano mirrors 141A and 141B are controlled to scan the signal light LS. The display part 240A or the touch panel monitor 11 is controlled to display a tomographic image of the fundus oculi Ef formed by the image forming part 220 (and image processing part 230), based on the detecting signal output from the CCD 184 that has detected the interference light LC.

The zoom switch 307 is a switch operated to change the angle of view (zoom magnification) for photographing of the fundus oculi Ef. Every time this zoom switch 307 is operated, for example, 45 degree and 22.5 degree of photographing angles of view are set alternately. When this zoom switch 307 is operated, the controlling part 210 that has received the operation signal controls the variable magnifying lens driving mechanism (not shown). The variable magnifying lens driving mechanism moves the variable magnifying lens 124 in the optical axial direction for changing the photographing angle of view.

The image switching switch 308 is a switch operated to switch displaying images. When the image switching switch 308 is operated while a fundus oculi observation image (a two-dimensional image of the surface of the fundus oculi Ef based on the video signal from the imaging device 12) is displayed on the display part 240A or the touch panel monitor 11, the controlling part 210 that has received the operation signal controls the display part 240A or the touch panel monitor 11. The display part 240A or the touch panel monitor 11 is controlled to display the tomographic image of the fundus oculi Ef. On the other hand, when the image switching switch 308 is operated while a tomographic image of the fundus oculi is displayed on the display part 240A or the touch panel monitor 11, the controlling part 210 that has received the operation signal controls the display part 240A or the touch panel monitor 11. The display part 240A or the touch panel monitor 11 is controlled to display the fundus oculi observation image.

The fixation target switching switch 309 is a switch operated to switch the position of the internal fixation target displayed by the LCD 140 (i.e. the projection position of the internal fixation target on the fundus oculi Ef). By operating this fixation target switching switch 309, the display position of the internal fixation target can be switched, for example, among "fixation position to capture the image of the peripheral region of the center of the fundus oculi," "fixation position to capture the image of the peripheral region of macula lutea" and "fixation position to capture the image of the peripheral region of papilla," in a circulative fashion. The controlling part 210 controls the LCD 140, in response to the operation signal from the fixation target switching switch 309, so as to display the internal fixation target in different positions on its display surface. Incidentally, the display positions of the internal fixation target corresponding to the above three fixation positions are, for example, preset based on clinical data or set for each eye E (image of the fundus oculi Ef) in advance.

The fixation target position adjusting switch 310 is a switch operated to adjust the display position of the internal fixation target. This fixation target position adjusting switch 310 is provided with, for example, an upward movement switch for upwardly moving the display position of the internal fixation target, a downward movement switch for downwardly moving the display position, a leftward movement switch for moving the display position leftward, a rightward movement switch for moving the display position rightward, and a reset switch for moving the display position to a predetermined initial position (default position). When receiving the operation signal from one of these switches, the controlling part 210 controls the LCD 140 so as to move the display position of the internal fixation target, in response to this operation signal.

The fixation target size switching switch 311 is a switch operated to change the size of the internal fixation target. When this fixation target size switching switch 311 is operated, the controlling part 210 that has received the operation signal changes the display size of the internal fixation target displayed on the LCD 140. The display size of the internal fixation target can be changed, for example, between "normal size" and "enlarged size," alternately. As a result, the size of the projection image of the fixation target projected onto the fundus oculi Ef is changed. When receiving the operation signal from the fixation target size switching switch 311, the controlling part 210 controls the LCD 140 in response to the operation signal, thereby changing the display size of the internal fixation target.

The mode switching knob 312 is a knob rotationally operated to select various types of photographing modes (such as a fundus oculi photographing mode to photograph a two-dimensional image of the fundus oculi, a B-scan mode to perform B-scan of the signal light LS, and a three-dimensional scan mode to make the signal light LS scan three-dimensionally). Also, this mode switching knob 312 may be capable of selecting a replay mode to replay a captured two-dimensional image or tomographic image of the fundus oculi Ef. Also, the mode switching knob 312 may be capable of selecting a photographing mode to control so that the photographing of the fundus oculi Ef is performed immediately after scan of the signal light LS. Control for performing each of the modes is executed by the controlling part 210.

A feature of control of the scanning signal light LS by the controlling part 210 and a feature of the process to the detecting signal from the OCT unit 150 by the image forming part 220 and the image processing part 230 will be respectively described below. An explanation regarding the process by the image forming part 220, etc., to the video signal from the fundus camera unit 1A will be omitted because it is the same as the conventional process.

Regarding the Signal Light Scanning

Scanning of signal light LS is performed by changing the facing directions of the reflecting surfaces of the Galvano mirrors 141A and 141B of the scanning unit 141 in the fundus camera unit 1A. By controlling the mirror drive mechanisms 241 and 242 respectively, the controlling part 210 changes the facing directions of the reflecting surfaces of the Galvano mirrors 141A and 141B, and scans the signal light LS on the fundus oculi Ef.

Once the facing direction of the reflecting surface of the Galvano mirror 141A is changed, the signal light LS is scanned in a horizontal direction (x-direction in FIG. 1) on the fundus oculi Ef. Whereas, once the facing direction of the reflecting surface of the Galvano mirror 141B is changed, the signal light LS is scanned in a vertical direction (y-direction in FIG. 1) on the fundus oculi Ef. Furthermore, by changing the facing directions of the reflecting surfaces of both the Galvano mirrors 141A and 141B simultaneously, the signal light LS may be scanned in the composed direction of x-direction and y-direction. That is, by controlling these two Galvano mirrors 141A and 141B, the signal light LS may be scanned in an arbitrary direction on the xy plane.

Figure 8A:
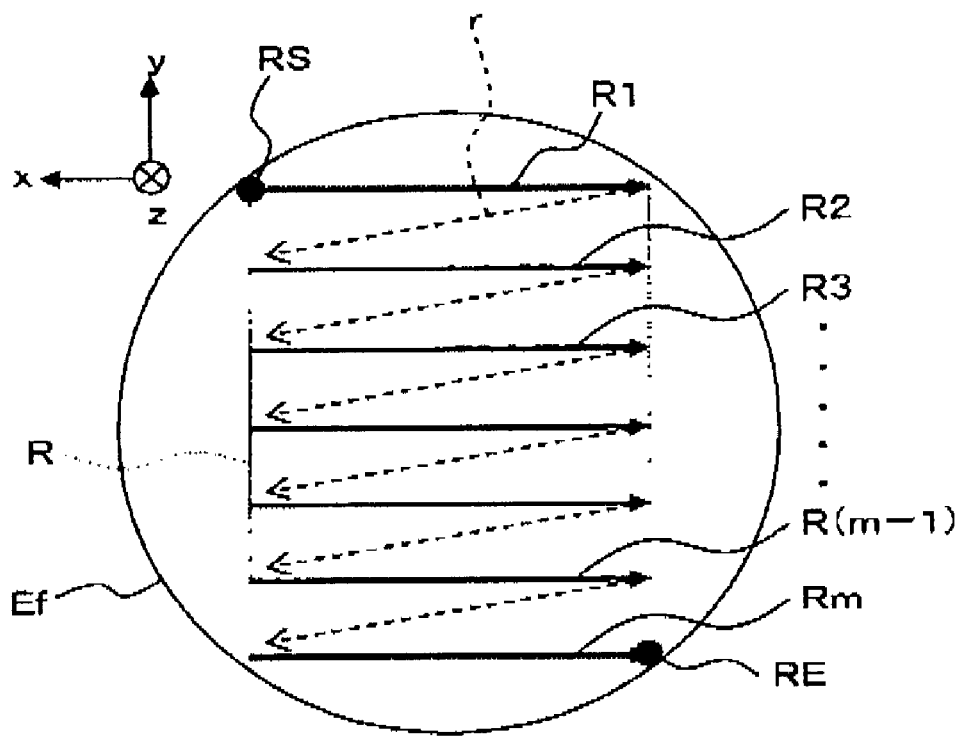
FIG. 8A represents one example of the scanning features of signal light when a fundus oculi is seen from the incident side of the signal light with respect to an eye.
Figure 8B:
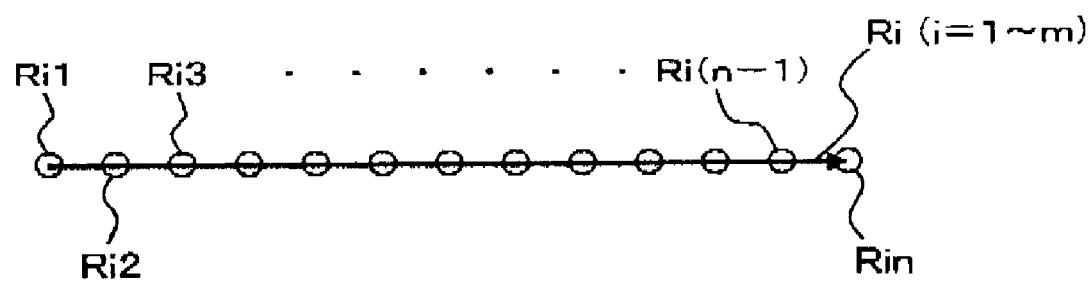
FIG. 8B represents one example of arrangement features of scanning points on each scanning line.

FIG. 8 represents one example of a feature of scanning of the signal light LS for forming an image of the fundus oculi Ef. FIG. 8A represents one example of a feature of scanning of the signal light LS, when the signal light LS sees the fundus oculi Ef from an incident direction onto the eye E (that is, +direction of z is seen from −direction of z in FIG. 1). Further, FIG. 8B represents one example of a feature of arrangement of scanning points (positions at which image measurement is carried out) on each scanning line on the fundus oculi Ef.

As shown in FIG. 8A, the signal light LS is scanned within a preset rectangular-shaped scanning region R. Within this scanning region R, plural (m number of) scanning lines R1 through Rm are set in the x-direction. When the signal light LS is scanned along each scanning line Ri (i=1 through m), detection signals of interference light LC are generated.

Herein, the direction of each scanning line Ri is referred to as the "main scanning direction" and the direction orthogonal thereto is referred to as the "sub-scanning direction". Therefore, the scanning of the signal light LS in the main scanning direction is performed by changing the facing direction of the reflecting surface of the Galvano mirror 141A, and the scanning in the sub-scanning direction is performed by changing the facing direction of the reflecting surface of the Galvano mirror 141B.

On each scanning line Ri, as shown in FIG. 8B, plural (n number of) of scanning points Ri1 through Rin are preset.

In order to execute the scanning shown in FIG. 8, firstly, the controlling part 210 controls the Galvano mirrors 141A and 141B to set the incident target of the signal light LS with respect to the fundus oculi Ef at a scan start position RS scanning point R11) on the first scanning line R1. Subsequently, the controlling part 210 controls the low coherence light source 160 so as to flush the low coherence light L0 and make the signal light LS enter into the scan start position RS. The CCD 184 receives the interference light LC based on the fundus reflection light of this signal light LS at the scan start position RS, and outputs the detection signal to the controlling part 210.

Next, by controlling the Galvano mirror 141A, the controlling part 210 scans the signal light LS in the main scanning direction and sets the incident target at a scanning point R12, triggering a flush emission of the low coherence light L0 for making the signal light LS enter into the scanning point R12. The CCD 184 receives the interference light LC based on the fundus reflection light of this signal light LS at the scanning point R12, and then outputs the detection signal to the controlling part 210.

Likewise, the controlling part 210 obtains detection signals output from the CCD 184 in response to the interference light LC with respect to each scanning point, by flushing the low coherence light L0 at each scanning point while shifting the incident target of the signal light LS from a scanning point R13 to R14, - - -, R1 (n−1) and R1n in order.

When the measurement at the last scanning point R1n on the first scanning line R1 is finished, the controlling part 210 controls the Galvano mirrors 141A and 141B simultaneously, and shifts the incident target of the signal light LS to the first scanning point R21 on the second scanning line R2 along a line switching scan r. Then, by conducting the above-described measurement with regard to each scanning point R2j (j=1 through n) on the second scanning line R2, a detection signal corresponding to each scanning point R2j is obtained.

Likewise, by conducting the measurement with respect to the third scanning line R3, - - -, the (m−1)th scanning line R (m−1) and the mth scanning line Rm, respectively, the detection signal corresponding to each scanning point is obtained. Symbol RE on the scanning line Rm is a scan end position corresponding to a scanning point Rmn.

As a result, the controlling part 210 obtains (m×n) number of detection signals corresponding to (m×n) number of scanning points Rij (i=1-m, j=1-n) within the scanning region R. Hereinafter, a detection signal corresponding to the scanning point Rij may be denoted by Dij.

Such interlocking control of shifting of scanning points and emission of the low coherence light L0 may be realized by synchronizing, for instance, timing of transmitting control signals to the mirror drive mechanisms 241 and 242 and the timing of transmitting control signals (output request signal) to the low coherence light source 160.

As described above, when each Galvano mirror 141A and 141B is operated, the controlling part 210 stores the position of each scanning line Ri or the position of each scanning point Rij (coordinates on the xy coordinate system) as information indicating the content of the operation. This stored content (scan positional information) is used in an image forming process as in the conventional device.

Regarding Image Processing

Next, one example of a process to OCT images (tomographic images of the fundus oculi Fe) by the image forming part 220 and the image processing part 230 will be described.

The image forming part 220 executes a process for formation of tomographic images of the fundus oculi Ef along each scanning line Ri (main scanning direction). The image processing part 230 executes a process for formation of a three-dimensional image of the fundus oculi Ef based on the tomographic images formed by the image forming part 220.

The tomographic image formation process by the image forming part 220, as in the conventional device, includes two steps of arithmetic processes. In the first step of arithmetic process, based on a detection signal Dij corresponding to each scanning point Rij, an image in the depth-wise direction (z-direction in FIG. 1) of the fundus oculi Ef at the scanning point Rij is formed.

Figure 9:
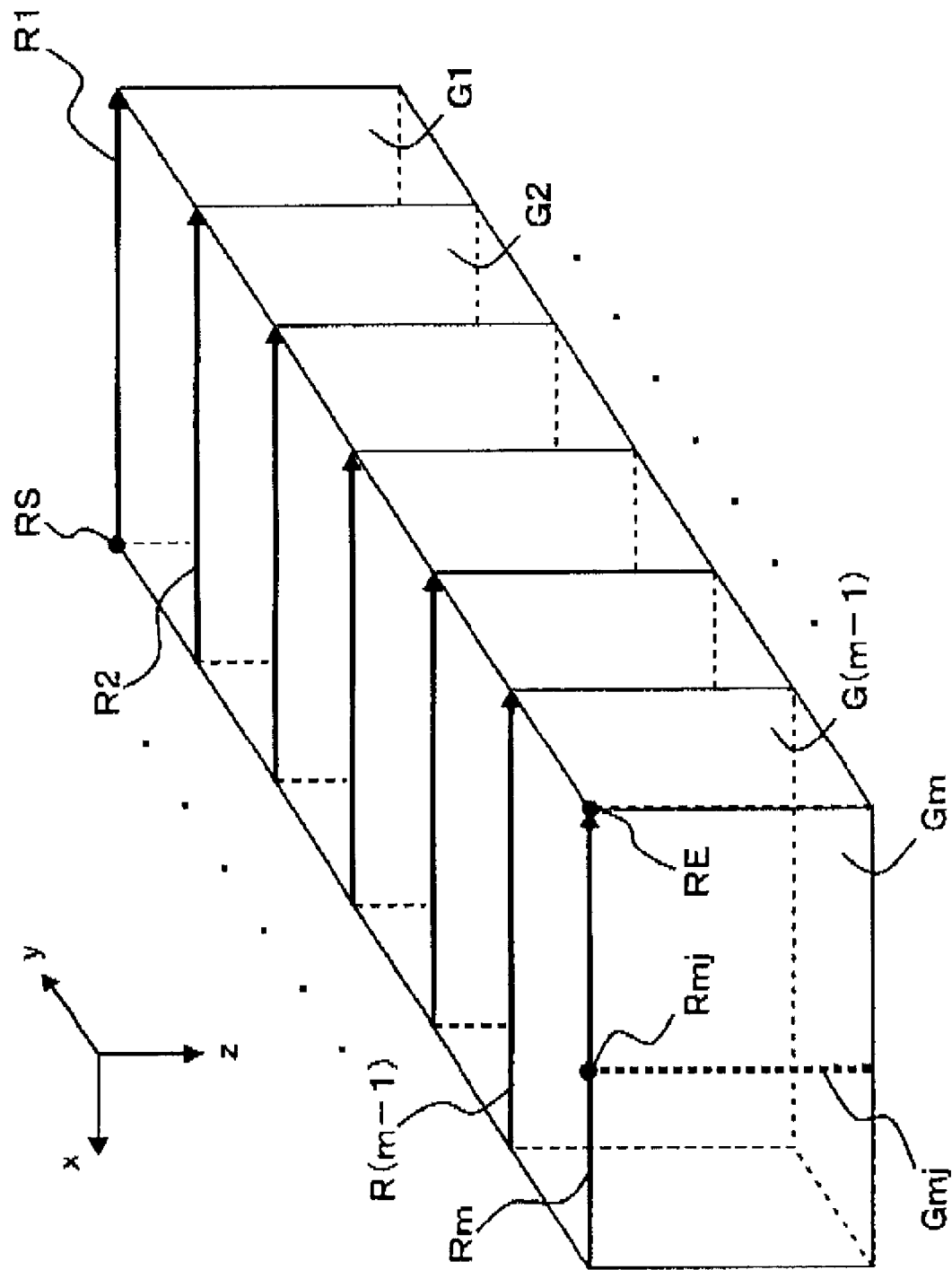
FIG. 9 is a schematic diagram representing one example of the scanning features of signal light and features of a tomographic image formed along each scanning line in a preferred embodiment of the fundus observation device related to the present invention.

FIG. 9 represents a feature of (a group of) tomographic images formed by the image forming part 220. In the second step of arithmetic process, with regard to each scanning line Ri, based on the images in the depth-wise direction at the n number of scanning points Ri1-Rin on the scanning line, a tomographic image Gi of the fundus oculi Ef along this scanning line Ri is formed. Then, the image forming part 220 determines the arrangement and interval of the scanning points Ri1-Rin while referring to the positional information (the aforementioned scan positional information) of the scanning points Ri1-Rin, and forms this scanning line Ri.

Through the above process, m number of tomographic images (a group of tomographic images) G1-Gm at different positions in the sub-scanning direction (y-direction) are obtained. The image data of the m number of tomographic images G1-Gm corresponds to the image data Ga of the tomographic image shown in FIG. 7 (to be described later).

Next, a process for formation of a three-dimensional image of the fundus oculi Ef by the image processing part 230 will be explained. A three-dimensional image of the fundus oculi Ef is formed based on the m number of tomographic images obtained through the above arithmetic processes. The image processing part 230 forms a three-dimensional image of the fundus oculi Ef by performing a known interpolating process to interpolate an image between the adjacent tomographic images Gi and G (i+1).

At this moment, the image processing part 230 determines the arrangement and interval of the scanning lines Ri with reference to the positional information of the respective scanning lines Ri, thereby forming the three-dimensional image. For this three-dimensional image, a three-dimensional coordinate system (x, y, z) is set up, based on the positional information (the aforementioned scan positional information) of the respective scanning points Rij and the z coordinate in the images of the depth-wise direction.

Further, the image processing part 230 is capable of, based on this three-dimensional image, forming a tomographic image of the fundus oculi Ef at a cross-section in an arbitrary direction other than the main scanning direction (x-direction). When the cross-section is designated, the image processing part 230 specifies the positions of the respective scanning points (and/or the interpolated image in the depth-wise direction) on this designated cross-section, and extracts an image (and/or the interpolated image in the depth-wise direction) in the depth-wise direction at each specified position from the three-dimensional image, thereby forming a tomographic image of the fundus oculi Ef at the designated cross-section by arranging plural extracted images in the depth-wise direction.

An image Gmj shown in FIG. 9 represents an image in the depth-wise direction (z-direction) at the scanning point Rmj on the scanning line Rm. Likewise, an image in the depth-wise direction at each scanning point Rij on the scanning line Ri, the image being formed through the first step of arithmetic process, may be represented as "image Gij."

Detailed Configuration of the Arithmetic and Control Unit

Detailed configuration of the arithmetic and control unit 200 will be described with reference to FIG. 7. Herein, the configuration of the controlling part 210 and image processing part 230 of the arithmetic and control unit 200 will be described.

The controlling part 210 is provided with a main controller 211, and an image storage part 212.

Further, the image processing part 230 is provided with an accumulated image generating part 231, a vascular territory extracting part 232, a vascular territory aligning part 233, a vascular cross sectional region specification part 234, an image interpolating part 235, and a layer thickness calculation part 236. The respective parts composing the control part 210 and the image processing part 230 will be described below.

Main Controller

The main controller 211 of the controlling part 210 comprises a microprocessor 201, and controls the respective parts of the fundus observation device 1 (previously described).

Image Storage Part

The image storage part 212 stores image data 212a of a two-dimensional image of the surface of the fundus oculi Ef (fundus oculi image Ef') formed by the image forming part 220 and image data Ga of a tomographic image. A process for storing image data to the image storage part 212 and a process for reading out image data from the image storage part 212 are performed by the main controller 211. The image storage part 212 includes a storing device such as a hard disk drive 204.

Incidentally, the image data 212a of the fundus oculi image Ef' and the image data Ga of a tomographic image shall have been captured almost at the same time. Herein, "captured almost at the same time" shall mean that both the image data have been captured at most with little time difference such as the case where both the image data have been captured at the same time, the case where one image data has been captured immediately after the other image data has been captured, and the case where both the image data have been captured in a series of examination processes.

Accumulated Image Generating Part

The accumulated image generating part 231 execute a process for generating an image obtained by accumulating tomographic images formed by the image forming part 220 in the depth-wise direction (z-direction) (an accumulated image), and functions as one example of the "accumulating part" in the present invention. To be more specific, the accumulated image generating part 231 accumulates the depth-wise images Gij composing the tomographic image in the depth-wise direction, thereby forming a dot image.

Here, "accumulating in the depth-wise direction" refers to an arithmetic process of summing, in the depth-wise direction, brightness values (pixel values) at the respective depth positions of the depth-wise images Gij (projecting). Therefore, the dot image obtained by accumulating the depth-wise image Gij has a brightness value, which is the sum of brightness values at the respective z positions of the depth-wise images Gij in the depth-wise direction.

The accumulated image generating part 231, for each of m pieces of tomographic images G1-Gm obtained with a series of scans of the signal light LS (see FIG. 9), forms an accumulated image comprising (m×n) pieces of dot images that are two-dimensionally distributed in the scanning region R of the signal light LS when m pieces of tomographic images G1-Gm are captured, by accumulating the respective depth-wise images Gij that form the tomographic image Gi in the depth-wise direction. This accumulated image becomes an image to represent the state of the surface of the fundus oculi Ef as with the fundus oculi image Ef' in such scanning region R (a two-dimensional image of a fundus oculi surface). The accumulated image is described in detail by the present inventors in Japanese Patent Application No. 2005-337628.

Vascular Territory Extracting Part

The vascular territory extracting part 232 extracts an image region corresponding to a fundus oculi vessel (a first vascular territory) from the fundus oculi image Ef', which is formed by the image forming part 220 (the fundus oculi image forming board 208a). Also, the vascular territory extracting part 232 extracts an image region corresponding to a fundus oculi vessel (a second vascular territory) from the accumulated image generated by the accumulated image generating part 231. This vascular territory extracting part 232 functions as one example of the "extraction part" of the present invention.

The extraction of the vascular territory by the vascular territory extracting part 232 may be performed using a well-known technique. For example, a boundary region between the vascular territory and the other region is detected by analyzing pixel values of the fundus oculi image Ef' (or accumulated image) and calculating a difference from the pixel value of an adjacent pixel to search for a pixel having a larger difference than a predetermined value. Consequently, the vascular territory is extracted from the fundus oculi image Ef' (or accumulated image). This extraction process utilizes the difference in pixel values (brightness values, etc.) between the vascular territory and the other region in the fundus oculi image Ef' or the accumulated image.

Since the fundus oculi image Ef' including the vascular territory is a relatively clear image, the vascular territory can be extracted down to detail. On the other hand, since the accumulated image is a relatively unclear image, the vascular territory is extracted in an unclear state as well; therefore, it is general that the details of the vascular territory cannot be extracted.

Vascular Territory Aligning Part

The vascular territory aligning part 233 aligns the first vascular territory extracted from the fundus oculi image Ef' and the second vascular territory extracted from the accumulated image by the vascular territory extracting part 232, and functions as one example of the "aligning part" of the present invention. This aligning process is alignment of the first and second vascular territories in the above-mentioned x-y direction, and a well-known pattern matching method can be used, for example.

Vascular Cross Sectional Region Specification Part

The vascular cross sectional region specification part 234 specifies the position of an image region corresponding to a cross section of a fundus oculi vessel (a vascular cross sectional region) in each of the tomographic images as the basis of the accumulated image based on the first and second vascular territories having been aligned by the vascular territory aligning part 233.

Therefore, the vascular cross sectional region specification part 234 operates so as to specify the position in the tomographic image corresponding to the vascular territory of the fundus oculi image EF' having been aligned with the vascular territory of the accumulated image, as the position of the vascular cross sectional region.

This process will be described in detail. As described above, the accumulated image is captured by accumulating m pieces of tomographic images G1-Gm in the depth-wise direction (z direction), and generally includes an unclear vascular territory (second vascular territory). As for this accumulated image, the position of each pixel is defined with x-y coordinate system corresponding to a scanning region R when the tomographic images G1-Gm are captured.

On the other hand, a two-dimensional X-Y coordinate system is predefined on the imaging surface of the imaging element 10a (12a) of the imaging device 10 (12) (not shown). In the fundus oculi image Ef' taken by the imaging device 10, the position of each pixel is defined with the X-Y coordinate system. This X-Y coordinate system defines a plane parallel to the x-y plane formed by the x-y coordinate system.

However, the scale of the coordinates in the x-y coordinate system (the length of a unit distance) may be same as or different from the scale of the coordinates in the X-Y coordinate system. Further, the directions of the coordinate axes of these two coordinate systems may coincide with each other or not coincide with each other. Generally, in a case where the scales and the directions of the coordinate axes of the two coordinate systems are different, it is possible to make the directions of the coordinate axes coincide by parallel displacement and rotational displacement, and it is possible to make the scales coincide by scaling the unit distances of the coordinate axes (that is, it is possible to transform the coordinates uniquely and reversibly).

Further, as described above, the z coordinate (Z coordinate; not shown) in which the depth-wise direction of the fundus oculi Ef is normal direction is defined in the orthogonal direction to the x-y plane (X-Y plane). Also, the scales in the z coordinate and the Z coordinate may be same or different (it is possible to make the scales coincide by scaling the unit distances of the coordinate axes). In the following, it is assumed that the directions of the respective coordinate axes coincide between the X-Y-Z coordinate system and the x-y-z coordinate system, and that the scales of the respective coordinate axes are equal (it is possible to thus assume because of the existence of the unique and reversible coordinate transformation).

The above-described vascular territory alignment part 233 performs alignment of the vascular territory in the fundus oculi image Ef' expressed by the X-Y coordinate system (first vascular territory) and the vascular territory in the accumulated image expressed by the x-y coordinate system (second vascular territory). That is, the vascular territory alignment part 233 performs the association of the position on the first vascular territory with the position on the second vascular territory.

The vascular cross sectional region specification part 234 specifies the position of the vascular cross sectional region in each of the tomographic images Gi (i=1–m) by executing, for example, the following processes. First, the vascular cross sectional region specification part 234 obtains a region in the accumulated image corresponding to the position of the cross section of the tomographic image Gi and, with reference to the result of the aforementioned alignment, obtains a region in the fundus oculi image Ef' corresponding to the position of the cross section (referred to as the "corresponding cross sectional region").

Next, the vascular cross sectional region specification part 234 obtains a common region (referred to as the "corresponding vascular cross sectional region") of the corresponding cross sectional region and the vascular territory (second vascular territory) in the fundus oculi image Ef'. This process can be executed by, for example, with reference to pixels forming the corresponding cross sectional region and pixels forming the vascular territory, extracting pixels having common coordinate values.

Subsequently, the vascular cross sectional region specification part 234, with reference to the result of the aforementioned alignment, obtains a region in the accumulated image corresponding to the corresponding vascular cross sectional region (a region in the first vascular image), and specifies the position of a region in the tomographic image Gi corresponding to the obtained region, as the position of the intended vascular cross sectional region.

As in FIG. 21, the position of the vascular cross sectional region specified by the vascular cross sectional region specification part 234 represents the position of the image region corresponding to the cross section of the fundus oculi vessel in the tomographic image Gi. In a position directly under the image region of the fundus oculi vessel (a deeper position than the image region in the fundus oculi), an unclear image region resulting from the existence of the fundus oculi vessel exists (see FIG. 21). This unclear image region formed directly under the fundus oculi vessel is referred to as the "region directly under the vessel." Therefore, it is possible to consider the vascular cross sectional region specification part 234 specifies the position of the region directly under the vessel.

The vascular territory alignment part 233 and the vascular cross sectional region specification part 234 function as one example of the "specification part" of the present invention.

Image Interpolating Part

The image interpolating part 235 interpolates at least one of the layer region in the tomographic image Gi and the boundary region of the layer region, based on the position of the vascular cross sectional region specified by the vascular cross sectional region specification part 234, and functions as one example of the "interpolating part" of the present invention.

The "layer region" herein refers to an image region corresponding to a retina, a choroid and a sclera of the fundus oculi Ef, or an image region corresponding to various layers and membranes such as a pigmented layer of retina, a stratum neuroepitheliale, a nerve fiber layer and an internal limiting membrane. These image regions are expressed in the tomographic image Gi as layers. The "boundary region" refers to an image region corresponding to a boundary of the adjacent layer regions. The layer region and boundary region as objects of the interpolation are included in the region directly under the vessel of which the position is specified by the vascular cross sectional region specification part 234.

Figure 10:
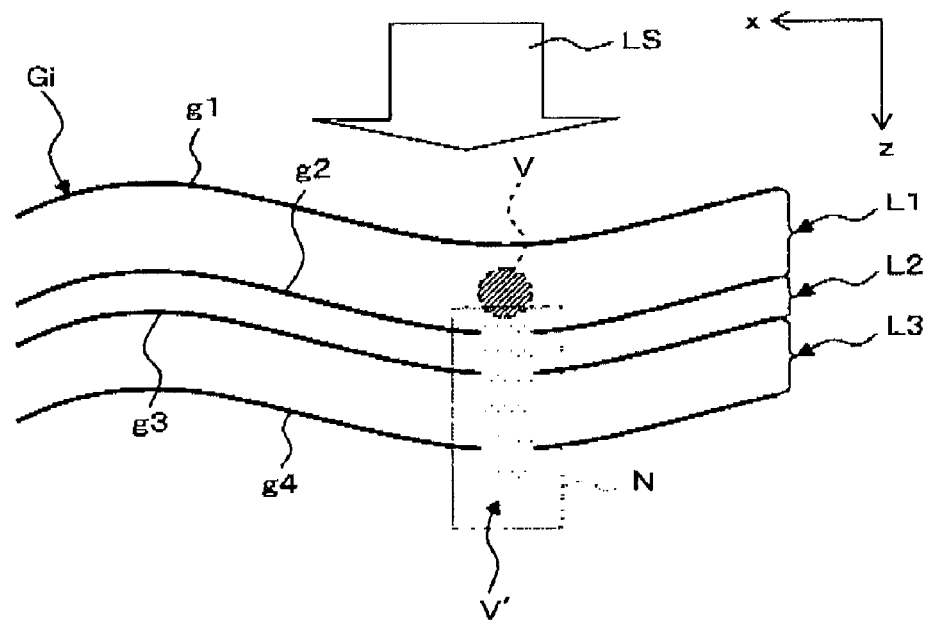
FIG. 10 is a schematic diagram for illustrating the interpolation of a layer region and a boundary region in a tomographic image according to the preferred embodiment of the fundus observation device according to the present invention.

One example of the interpolation by the image interpolating part 235 will be described with reference to FIGS. 10 and 11. Layer regions L1, L2, L3 and boundary regions g1, g2, g3, g4 are illustrated in the tomographic image Gi shown in FIG. 10. Symbol V in FIG. 10 denotes an image region corresponding to the fundus oculi vessel (the vascular cross sectional region), and symbol V' denotes an image region located directly under the vascular cross sectional region V (the region directly under the vessel). Further, symbol LS denotes signal light illuminated onto the fundus oculi Ef.

The positions of the vascular cross sectional region V and the region directly under the vessel V' in the tomographic image Gi may be automatically detected by the image processing part 230 (for example, by using threshold processing on a pixel value), or may be manually directed by a user (for example, by designating a region in an image by the mouse 206).

The image interpolating part 235 sets an image region N including the region directly under the vessel V' and a peripheral region thereof (hereafter, referred to as the "near field region"). The user may set the near field region N manually.

Next, the image interpolating part 235 obtains (image data of) the boundary regions g2, g3, g4 included in the near field region N. Consequently, the boundary regions g2, g3, g4 located in the peripheral region of the region directly under the vessel V' are obtained. The boundary regions g2, g3, g4 are previously extracted by the image processing part 230 as described above, and the image interpolating part 235 acts so as to obtain a portion included in the near field region N from the extracted boundary regions g2, g3, g4. Otherwise, the image interpolating part 235 may obtain the boundary regions g2, g3, g4 by, for example, analyzing the pixel value in the near field region N.

Subsequently, the image interpolating part 235 interpolates the boundary region in the region directly under the vessel V' based on the boundary regions g2, g3, g4 of the peripheral region. The interpolation of the boundary region g2 will be described. As shown in FIG. 11, the near field region N includes g21 (+x side in the region directly under the vessel V') and g22 (−x side in the region directly under the vessel V'), which are part of the boundary region g2 located in the peripheral region of the region directly under the vessel V'.

The image interpolating part 235 calculates inclination of each point in g21 and g22 that are part of the boundary region g2 (especially, inclination of each point contacting the region directly under the vessel V'). Then, the image interpolating part 235 calculates an image (image data) of the boundary region g2 in the region directly under the vessel V' to obtain g23 so as to match the calculated inclination. The inclination of the image g23 is set so that g23 connects smoothly to each of g21 and g22 that are part of the boundary region g2.

Figure 11:
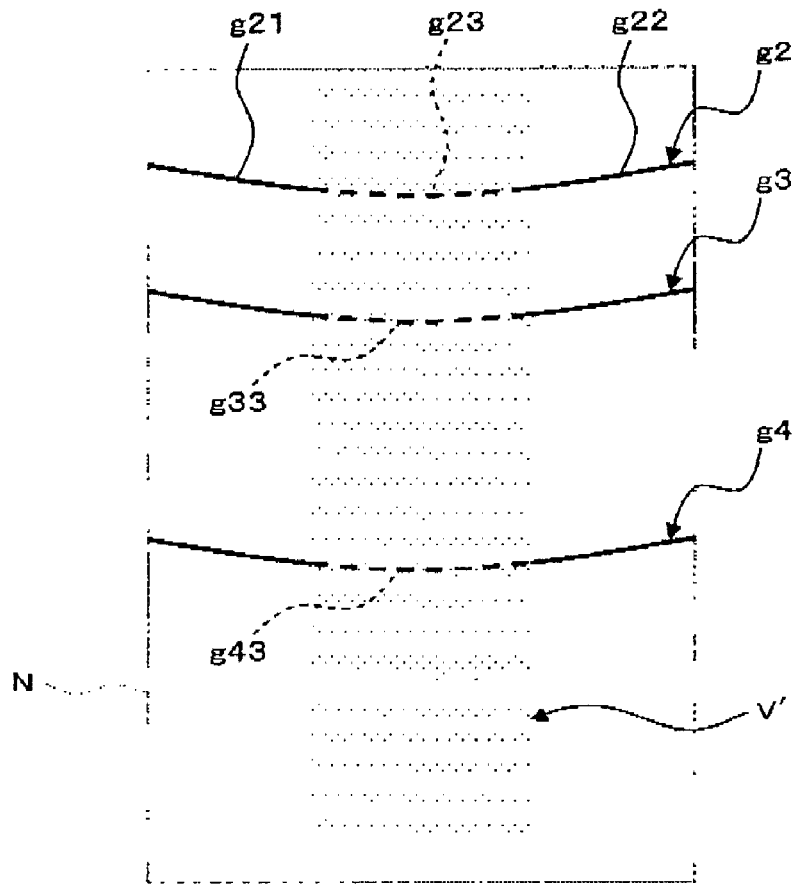
FIG. 11 is a schematic diagram for illustrating the interpolation of a layer region and a boundary region in a tomographic image according to the preferred embodiment of the fundus observation device according to the present invention.

The image interpolating part 235 calculates again on the boundary regions g3 and g4 to obtain an image g33 of the boundary region g3 and an image g43 of the boundary region g4 in the region directly under the vessel V' (see FIG. 11). That is a description of the interpolation of the boundary region.

Next, the interpolation of layer regions L1, L2, L3 will be described. The image interpolating part 235 obtains (image data of) an image of the layer region L1 in the region directly under the vessel V' based on the image data of the layer region L1 in the near field region N, by applying an arbitrary well-known interpolation method. The interpolation may use, for example, the same method as used when the image processing part 230 forms a three-dimensional image from m pieces of tomographic images.

Layer Thickness Calculation Part

The layer thickness calculation part 236 calculates the thickness of a layer region (thickness of a layer included in the fundus oculi Ef) based on the results of the interpolation of a boundary region and a layer region by the image interpolating part 235, and functions as one example of the "calculation part" of the present invention.

Figure 12:
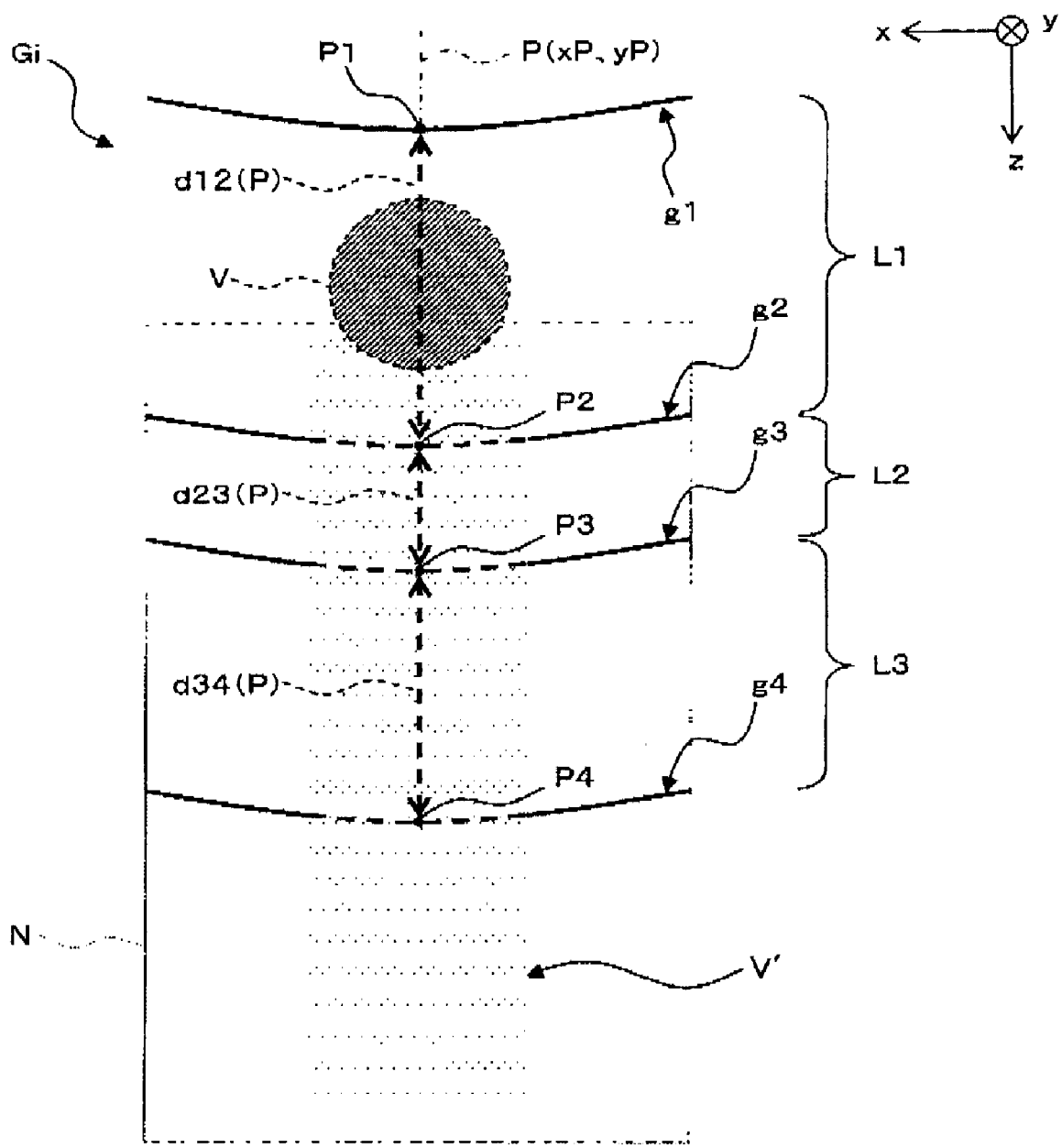
FIG. 12 is a schematic diagram for illustrating arithmetic processing of the thickness of a layer region according to the preferred embodiment of the fundus observation device according to the present invention.

A specific example of processes executed by the layer thickness calculation part 236 will be described with reference to FIG. 12. FIG. 12 shows an example of calculation of the thickness of a layer region at a position P (xP, yP) in the tomographic image Gi. Positions on the boundary regions g1, g2, g3 and g4 corresponding to the position P are denoted by P1 (xP, yP, z1), P2 (xP, yP, z2), P3 (xP, yP, z3) and P4 (xP, yP, z4), respectively.

The position P1 is specified as a position corresponding to coordinate values (xP, yP) in the boundary region g1. The positions P2-P4 are specified as positions corresponding to the coordinate values (xP, yP) in the images g23, g33, g34 of the boundary regions g2, g3, g4 obtained by the image interpolating part 235. The positions P2-P4 are positioned in the region directly under the vessel V'. In conventional arts, it was impossible to measure the thickness of the layer regions L1, L2, L3 at such a position P.

The layer thickness calculation part 236 obtains thickness d12(P)=|z2−z1| of the layer region L1 at the position P by calculating the distance between the positions P1 and P2. Similarly, the layer thickness calculation part 236 obtains thickness d23(P)=|z3−z2| of the layer region L2 at the position P by calculating the distance between the positions P2 and P3, and obtains thickness d34(P)=|z4−z3| of the layer region L3 at the position P by calculating the distance between the positions P3 and P4.

A distance between positions Pk and P (k+1) (k=1, 2, 3) may also be calculated by applying other methods whereby the distance is obtained by counting the number of pixels between the pixel at the position Pk and the pixel at the position P (k+1) and multiplying the counted result by the distance between pixels (well-known), instead of calculating dk (k+1)=|z(k+1)−zk| (that is, the difference in the z-coordinate values) as described above.

The layer thickness calculation part 236 calculates the thickness of a layer region (thickness of a layer) at the position corresponding to the region directly under the vessel V' as described above. On the other hand, the thickness of a layer region at a position other than the region directly under the vessel V' can be obtained by calculating the distance between boundary regions at the position as in conventional arts.

The image processing part 230 may be, for example, configured to be capable of measuring the distance between any two points in the tomographic image Gi or measuring the area of any image region, instead of measuring the thickness as described above. Further, the image processing part 230 may be configured to be capable of measuring the distance between any two points in a three-dimensional image or measuring the volume of any image region.

Operation

Figure 13:
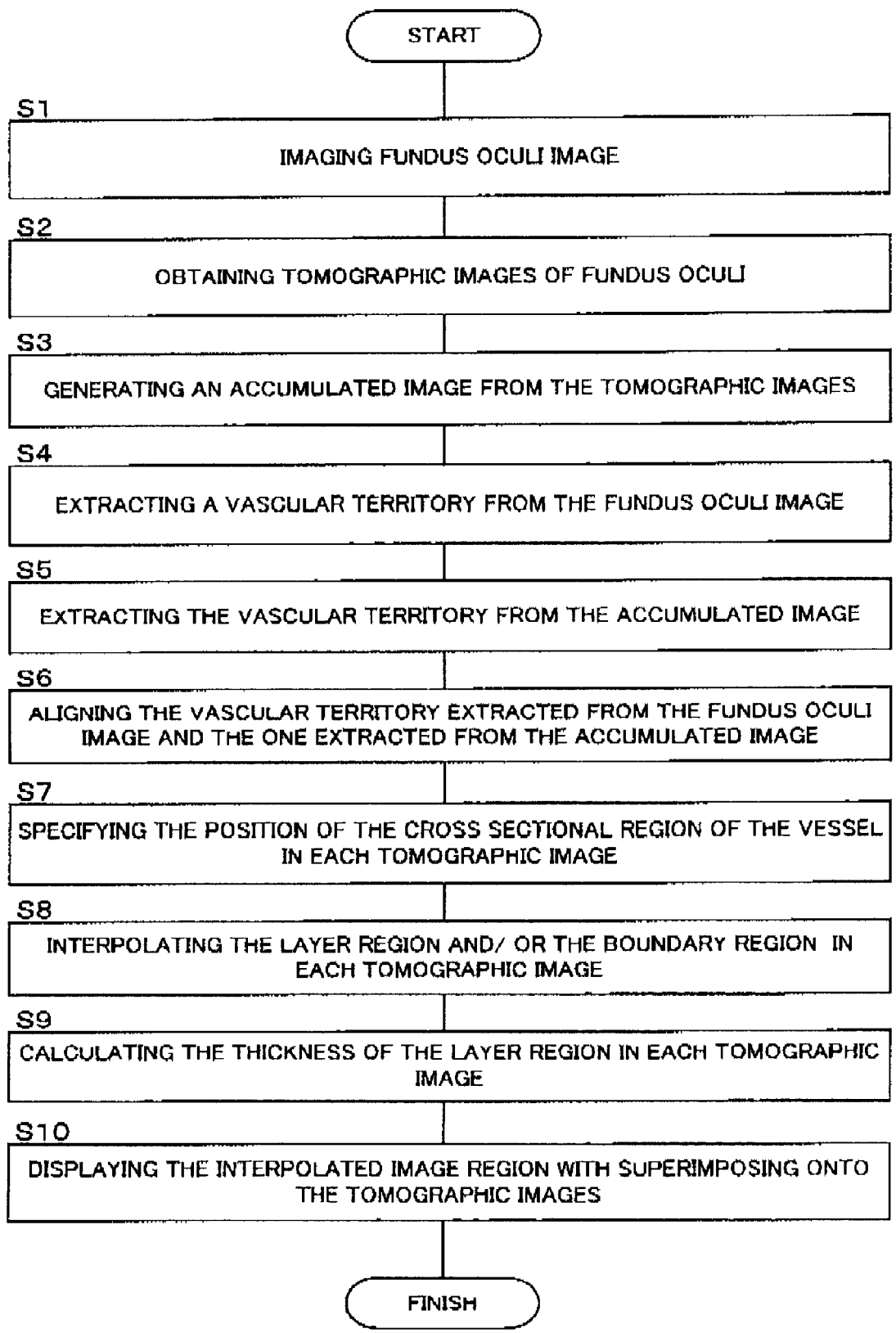
FIG. 13 is a flowchart that shows one example of the workings of the preferred embodiment of a fundus observation device related to the present invention.

The operation of the fundus observation device 1 having the above-described configuration will be described with reference to FIGS. 13-18. FIG. 13 is a flowchart representing one example of the operation of the fundus observation device 1. FIGS. 14-18 represent examples of various images displayed by the fundus observation device 1. These images are appropriately displayed on the display part 240A with the main controller 211.

First, the fundus oculi image Ef' of the fundus oculi Ef of the eye E is imaged (S1), and the tomographic images G1-Gm of the fundus oculi Ef are obtained (S2). Herein, the scanning region R of the signal right LS for obtaining the tomographic images G1-Gm is assumed to be set within the imaging region of the fundus oculi image Ef'. However, in the present invention, it is sufficient in general that the scanning region R be set within the region of the surface of the fundus oculi Ef corresponding to at least part of fundus oculi image Ef'. (Consequently, the scanning region R is set so as to have a common region with at least part of the imaging region of the fundus oculi image Ef', and hence, it becomes possible to execute an alignment process in step S6 described later.) Either imaging of the fundus oculi image Ef' or obtaining of the tomographic images G1-Gm may be performed first.

Figure 14:
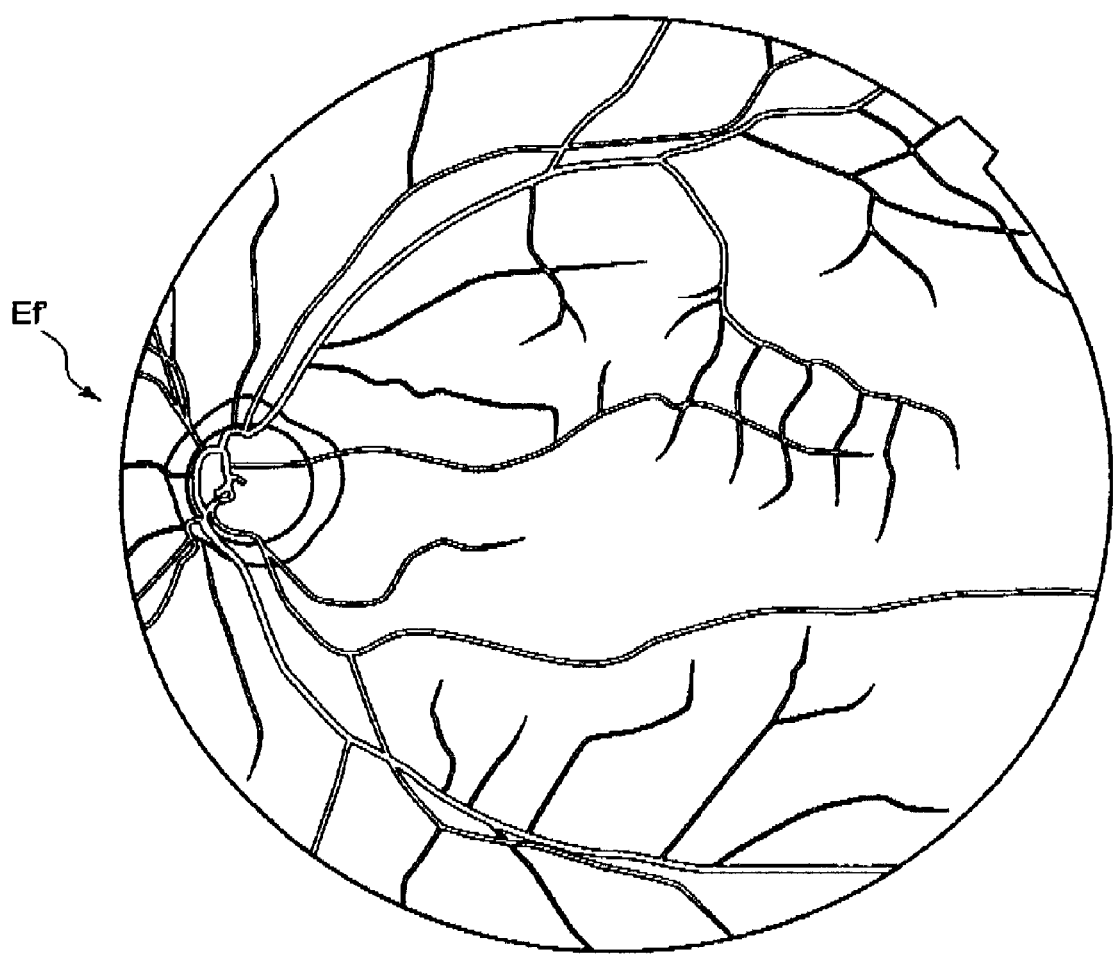
FIG. 14 is a view illustrating an example of the fundus oculi image obtained in the preferred embodiment of the fundus observation device according to the present invention.

FIG. 14 represents one example of the fundus oculi image Ef' imaged in step S1. This fundus oculi image Ef' is an image imaged as in a conventional fundus camera, and obtained as a relatively clear image as shown in FIG. 14.

Image data 212a of the fundus oculi image Ef' and image data Ga of the tomographic images G1-Gm are stored in the image storage part 212 with the main controller 211. The main controller 211 sends the image data 212a of the fundus oculi image Ef' and the image data Ga of the tomographic images G1-Gm to the image processing part 230.

The accumulated image generating part 231 of the image processing part 230 generates (image data of) an accumulated image Pr in which the tomographic images G1-Gm are accumulated in the depth-wise direction, based on the image data Ga (S3).

Figure 15:
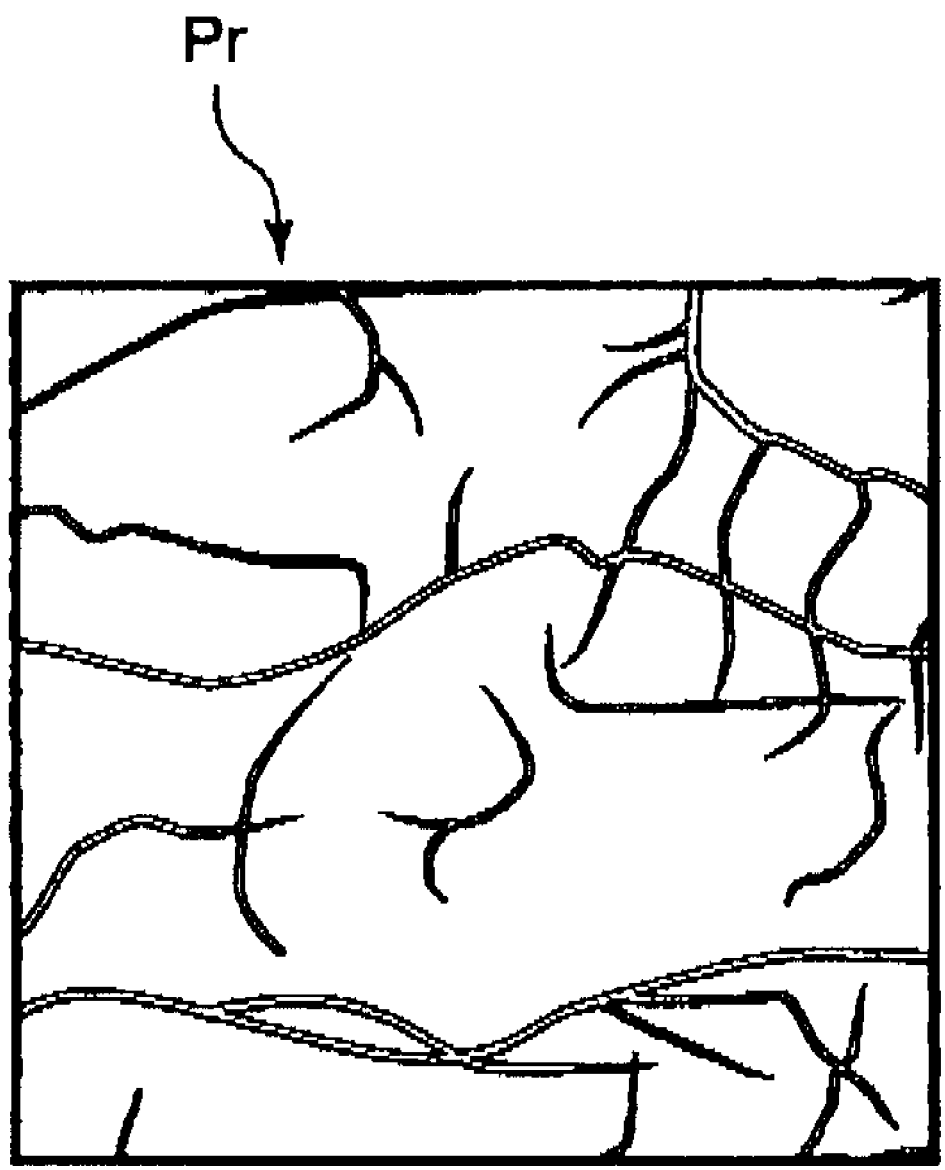
FIG. 15 is a view illustrating an example of an accumulated image generated in the preferred embodiment of the fundus observation device according to the present invention.

FIG. 15 represents one example of the accumulated image Pr generated in step S3. This accumulated image Pr is obtained as a relatively unclear image as described above. As described above, since the scanning region R for obtaining the tomographic images G1-Gm is set in the imaging region of the fundus oculi image Ef', the accumulated image Pr is an image representing a partial region (scanning region R) of the fundus oculi image Ef'.

The vascular territory extracting part 232 extracts a vascular territory W1 included in the fundus oculi image Ef' based on the image data 212a of the fundus oculi image Ef' (S4). Further, based on the image data of the accumulated image Pr generated in step S3, the vascular territory extracting part 232 extracts a vascular territory W2 included in the accumulated image Pr (S5). Either the extraction of the vascular territory W1 from the fundus oculi image Ef' or the extraction of the vascular territory W2 from the accumulated image Pr may be performed first.

Figure 16:
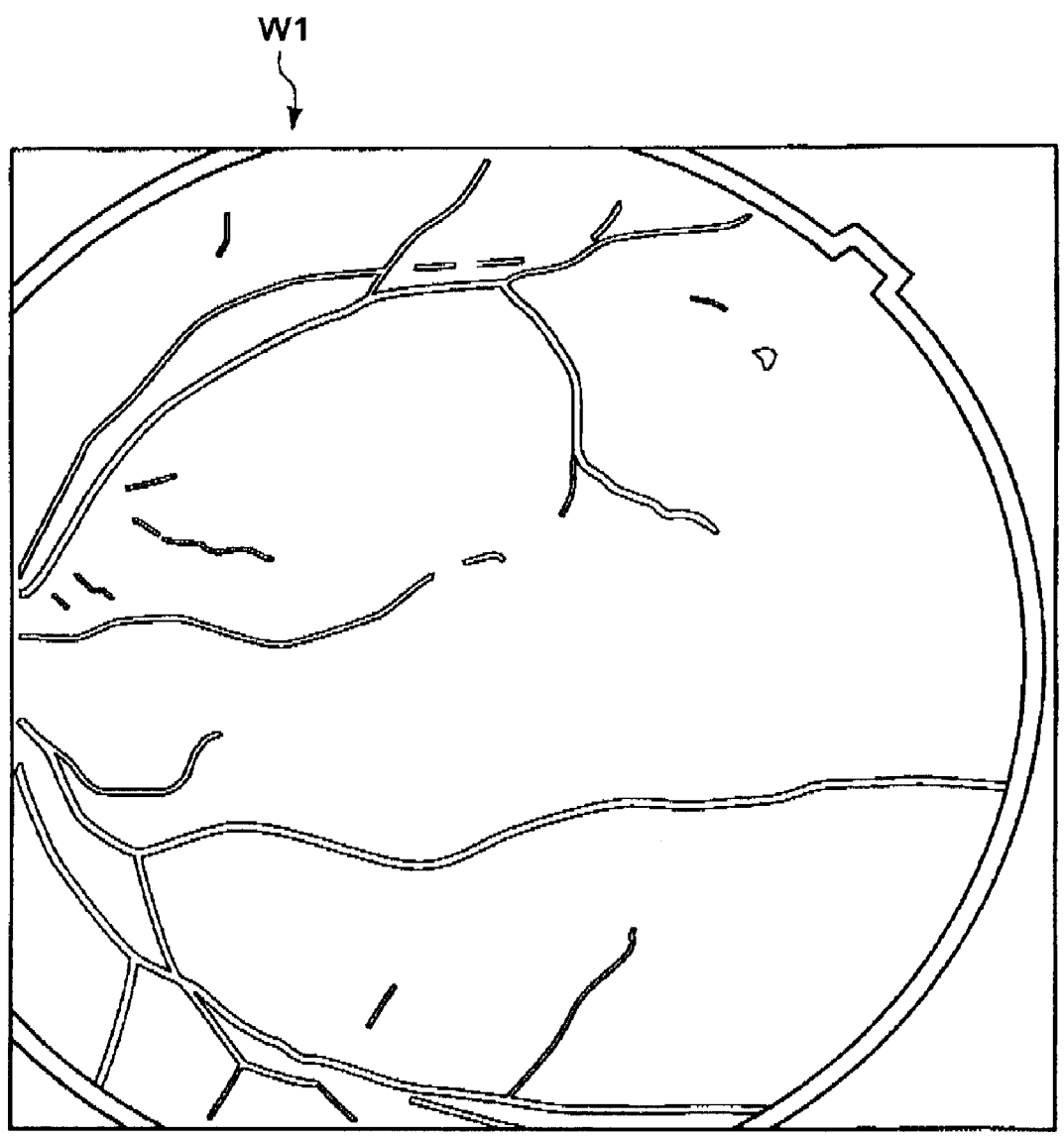
FIG. 16 is a view illustrating an example of a vascular territory extracted from the fundus oculi image in the preferred embodiment of the fundus observation device according to the present invention.

FIG. 16 shows one example of the vascular territory W1 of the fundus oculi image Ef' extracted in step S4. As described above, this vascular territory W1 is an image describing the imaging region corresponding to a vessel in the fundus oculi image Ef' down to relatively close detail (to thin vessels).

Figure 17:
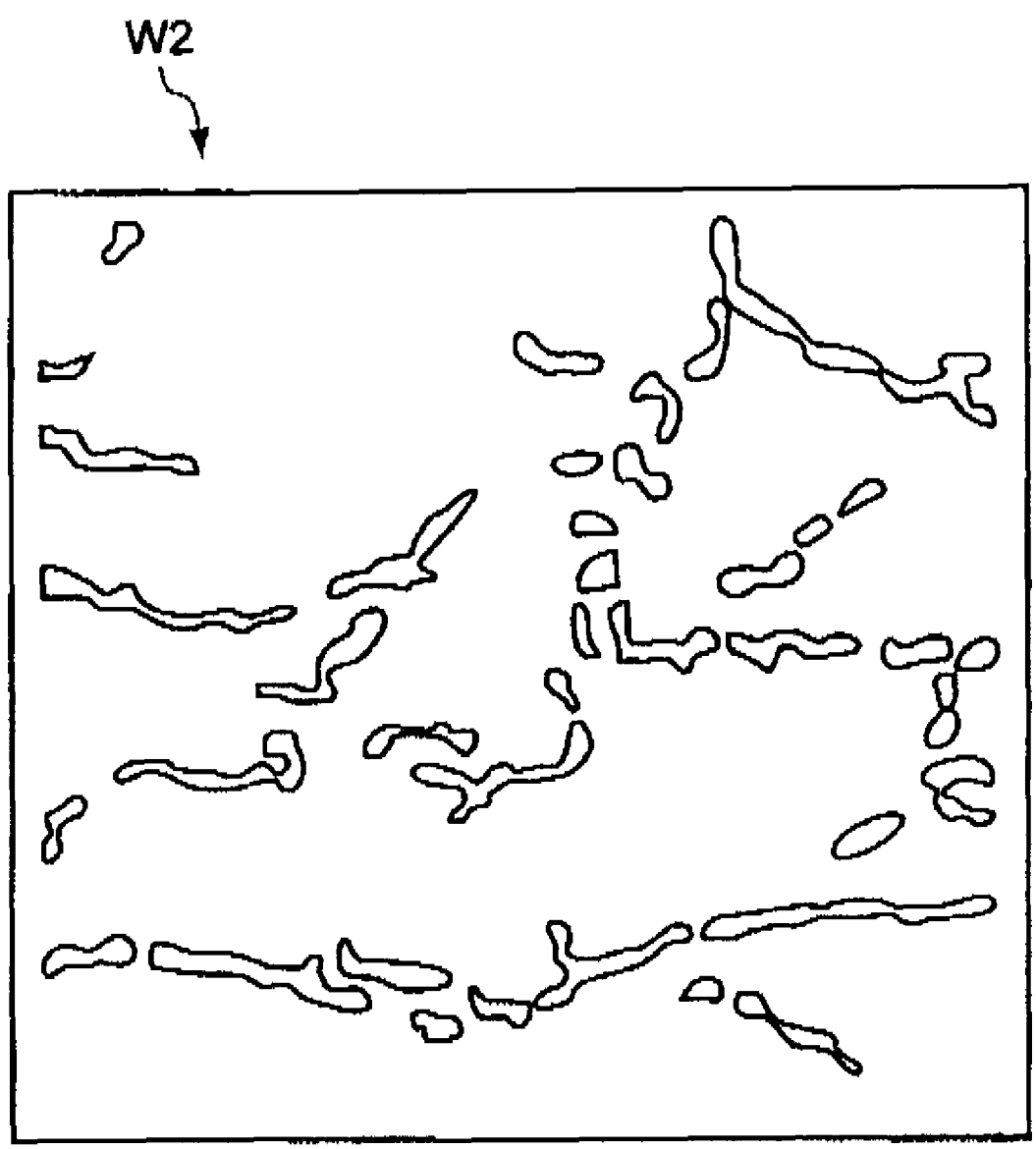
FIG. 17 is a view illustrating an example of a vascular territory extracted from the accumulated image in the preferred embodiment of the fundus observation device according to the present invention.

FIG. 17 shows one example of the vascular territory W2 of the accumulated image Pr extracted in step S5. This vascular territory W2 is extracted from the relatively unclear accumulated image Pr and, as shown in FIG. 17, is not an image describing an image region corresponding to a fundus oculi vessel down to detail (compared to the vascular territory W1 at least). As apparent from FIGS. 16 and 17, the vascular territory W2 of the accumulated image Pr may be obtained as an image with some portions thereof cut, and thus, may not clearly describes the state of the connection of fundus oculi vessels when compared to the vascular territory W1 of the fundus oculi image Ef'.

The vascular territory alignment part 233 aligns the vascular territory W1 extracted from the fundus oculi image Ef' with the vascular territory W2 extracted from the accumulated image Pr (S6). In order to shorten the processing time, the alignment may be performed after obtaining the (approximate) positional relation between the vascular territory W1 and the vascular territory W2 based on the positional relation between (the X-Y coordinate values of) the imaging region of the fundus oculi image Ef' and (the x-y coordinates of) the scanning region R.

Figure 18:
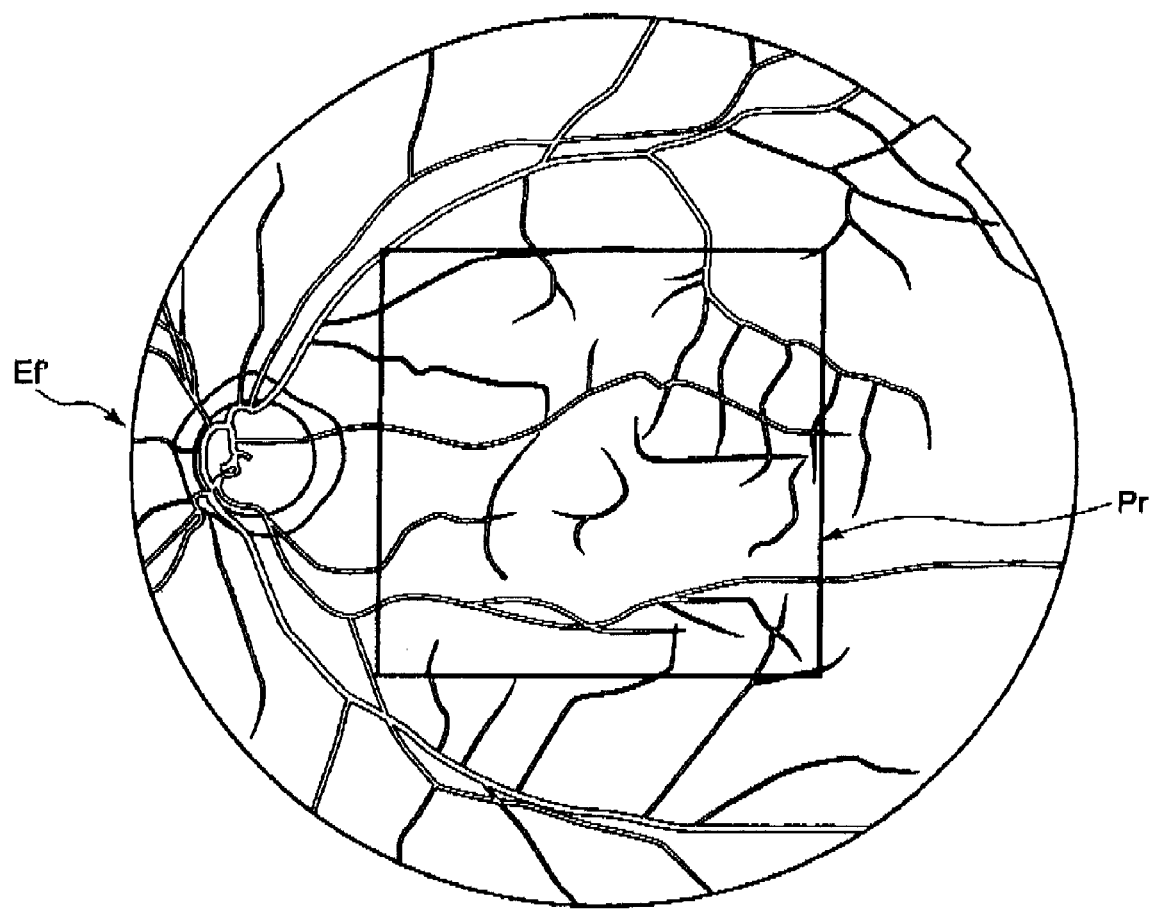
FIG. 18 is a view illustrating an example of the fundus oculi image and the accumulated image displayed in a superimposed state based on the results of vascular territory alignment in the preferred embodiment of the fundus observation device according to the present invention.

FIG. 18 shows one example of an image in which the fundus oculi image Ef' and the accumulated image Pr are superimposed based on the result of alignment of the vascular territories W1 and W2 executed in step S6. As apparent from FIG. 18, the fundus oculi image Ef' and the accumulated image Pr are suitably aligned by alignment of the vascular territories W1 and W2.

The vascular cross sectional region specification part 234 specifies the position of the vascular cross sectional region in the tomographic image Gi in each of the tomographic images G1-Gm as the basis of the accumulated image Pr, based on the two vascular territories W1 and W2 having been aligned with each other (S7).

The image interpolating part 235 interpolates the layer regions and/or the boundary regions of the layer regions in the tomographic image Gi based on the specified position of the vascular cross sectional region (S8).

The layer thickness calculation part 236 calculates the thickness of the layer region at the position corresponding to the region directly under the vessel and the thickness of the layer region at other positions, based on the interpolated boundary regions and layer regions (S9). The calculation results are stored in, for example, the hard disk drive 204 with the main controller 211.

The main controller 211 may form, for example, a map of the results of calculation of the thickness of the layer region, that is, distribution information on the thickness of the layer region corresponding to each position (x-y coordinate positions) of the fundus oculi Ef. The formed information are stored on the hard disk drive 204 or displayed on the display part 240A.

Further, the main controller 211 causes the display part 240A to display the image region (the layer region, the boundary region) interpolated in step S8 in the superimposed on the region directly under the vessel in the tomographic image Gi (S11). Consequently, the layers and boundaries, which are unclear as shown in FIG. 21 in conventional arts, are interpolated and clearly displayed.

Effect and Advantage

The actions and effects of the above-described fundus observation device 1 will be described. This fundus observation device 1 is configured to form the fundus oculi image Ef' of the fundus oculi Ef and also form the tomographic images G1-Gm of the fundus oculi Ef based on the data obtained by scanning a region (the scanning region R) of the surface of the fundus oculi Ef corresponding to at least a portion of the fundus oculi image Ef'. Moreover, the fundus observation device 1 is configured to generate the accumulated image Pr by accumulating these tomographic images G1-Gm in the depth-wise direction and also extract the vascular territories W1 and W2 from the accumulated image Pr and the fundus oculi image Ef', respectively. The fundus observation device 1 acts so as to specify the position of the vascular cross sectional region in each of the tomographic images G1-Gm based on the two vascular territories W1 and W2 having been extracted.

According to this fundus observation device 1, it becomes possible to ascertain the position of the vascular cross sectional region corresponding to the cross section of the vessel in the tomographic images G1-Gm of the fundus oculi Ef.

In specific, since the fundus observation device 1 is configured to specify the position of the vascular cross sectional region based on the vascular territory W1 (describing a relatively detailed state of the fundus oculi vessel) in the fundus oculi image Ef', it is also possible to suitably specify the position of the vascular cross sectional region corresponding to a vessel that is not clearly shown in the vascular region W2, which cannot describe a detailed condition and connection of the fundus oculi vessel, of the accumulated image Pr. Therefore, even if a vessel actually existing at the cross sectional position of the fundus oculi Ef corresponding to each of the tomographic images G1-Gm is not clearly described in the tomographic images G1-Gm or the accumulated image Pr, it is possible to specify the position of the vascular cross sectional region corresponding to this vessel.

Further, the fundus observation device 1 of the present embodiment acts so as to interpolate the layer region corresponding to the layer of the fundus oculi Ef positioned directly under the vascular cross sectional region and the boundary region corresponding to the layer boundary in each of the tomographic images G1-Gm, based on the position of the specified vascular cross sectional region. Consequently, it becomes possible to obtain the layer region and boundary region positioned directly under the vascular cross sectional region, which cannot be obtained in conventional arts.

Furthermore, according to this fundus observation device 1, it is possible to measure the thickness of the layer region directly under the vascular cross sectional region, which cannot be measured in conventional arts, based on the results of the interpolation of the layer region and the boundary region.

Besides, since it is possible to display the image region (the layer region, the boundary region) obtained by interpolation in the superimposed state on the tomographic images G1-Gm, observation of all of the tomographic images G1-Gm including the image directly under the vascular cross sectional region becomes possible.

According to the present embodiment, it is configured to form a two-dimensional image of surface of a fundus oculi, to form a tomographic image based on data obtained by scanning the region of the surface of the fundus oculi corresponding to at least part of the two-dimensional image, to generate an accumulated image by accumulating the tomographic images in the depth-wise direction, to extract vascular territories from this accumulated image and two-dimensional image, respectively, and to specify the position of a vascular cross sectional region in the tomographic image based on the two extracted vascular territories. Therefore, it becomes possible to ascertain the position of the vascular cross sectional region as the image region corresponding to the cross section of the vessel in the tomographic image of the fundus oculi.

Further, according to the present embodiment, it is configured to interpolate a layer region and a boundary region located directly under the vascular cross sectional region in the tomographic image based on the specified position of the vascular cross sectional region. Therefore, it is possible to obtain the previously unobtainable layer region and boundary region located directly under the vascular cross sectional region.

Furthermore, according to the present embodiment, the previously immeasurable thickness of the layer region directly under the vascular cross sectional region can be measured based on the results of the interpolation of the layer region and the boundary region.

MODIFIED EXAMPLE

The configuration described above is merely one example to preferably implement the fundus observation device related to the present invention. Therefore, optional modifications may be implemented appropriately within the scope of the present invention.

For example, the fundus observation device according to the present embodiment has a fundus camera (unit) as a device that forms two-dimensional images of the fundus oculi surface, but it may have a configuration in which a two-dimensional image of the fundus oculi surface is formed by using arbitrary opthalmological equipment such as a slit lamp biomicroscope.

Moreover, in the above embodiment, the image forming part 220 (the image forming board 208) executes a process for formation of a two-dimensional image and a tomographic image of the surface of the fundus oculi Ef, and the controlling part 210 (microprocessor 201, etc.) executes a process for various controls. However, it is possible to configure so as to execute both the processes by one or plural computers.

Furthermore, the opthalmologic image-processing program (control program 204a) according to the present invention can be stored on any computer-readable storage medium. Such storage medium may include an optical disk, a magnet-optical disk (e.g., CD-ROM, DVD-RAM, DVD-ROM, MO, etc.), a magnetic storage (hard disk, floppy™ disk, ZIP, etc.), and a semiconductor memory.

What is claimed is:

1. A fundus observation device comprising:
   a first image forming part configured to form a two-dimensional image of a surface of a fundus oculi of an eye based on optically obtained data;
   a second image forming part configured to form tomographic images of said fundus oculi based on data obtained by optically scanning a region of the surface of said fundus oculi corresponding to at least part of said two-dimensional image;
   an accumulated image generating part configured to generate an accumulated image by accumulating the formed tomographic images in a depth-wise direction;
   an extracting part configured to extract a first vascular territory corresponding to a fundus oculi vessel from said two-dimensional image formed by said first image forming part, and to also extract a second vascular territory corresponding to a fundus oculi vessel from said accumulated image generated by said accumulated image generating part;
   an alignment part configured to align said extracted first vasular territory with said extracted second vascular territory; and
   a specification part configured to specify a layer region or a boundary region between layer regions below the second vascular territory among regions of the tomographic images indicated by the first vascular territory, as a position of a vascular off region below a cross section of a fundus oculi vessel in the tomographic image when said extracted first vascular territory corresponds to said extracted second vascular territory as a result of the alignment.

2. A fundus observation device according to claim 1, further comprising an interpolating part configured to interpolate a boundary region corresponding to a layer boundary of the fundus oculi in the tomographic image based on the position of the vascular off region.

3. A fundus observation device according to claim 1, further comprising an interpolating part configured to interpolate a layer region corresponding to a layer of the fundus oculi in the tomographic image based on the position of the vascular off region.

4. A fundus observation device according to claim 2, further comprising a display part configured to display an image region obtained by said interpolation by said interpolating part in a superimposed state on the tomographic image formed by said second image forming part.

5. A fundus observation device according to claim 3, further comprising a display part configured to display an image region obtained by said interpolation by said interpolating part in a superimposed state on the tomographic image formed by said second image forming part.

6. A fundus observation device according to claim 2, further comprising a calculation part configured to calculate thickness of the layer included in said fundus oculi based on a result of said interpolation by said interpolating part.

7. A fundus observation device according to claim 3, further comprising a calculation part configured to calculate thickness of the layer included in said fundus oculi based on a result of said interpolation by said interpolating part.

8. A fundus observation device according to claim 1, wherein said specification part comprises an aligning part configured to align said first vascular territory and said second vascular territory extracted by said extracting part, and a position in said tomographic image corresponding to said first vascular territory aligned with said second vascular territory is specified as a position of the vascular off region.

9. A fundus observation device according to claim 1, wherein said second image forming part comprises:
   a light source;
   an interference light generating part configured to split light output from the light source into signal light that travels toward said fundus oculi and reference light that travels toward a reference object, and also generate interference light by superposing the signal light passed through said fundus oculi and the reference light passed through said reference object;
   a detecting part configured to receive the generated interference light and output a detection signal; and
   a scanning part configured to scan an incident position of said signal light to said fundus oculi in a predetermined main scanning direction and a sub scanning direction orthogonal to the main scanning direction,
   wherein, for each of a plurality of said incident positions along said main scanning direction, an image in the depth-wise direction of said fundus oculi in the incident position is formed based on said detection signal based on the interference light generated with the signal light and reference light passed through the incident position, and a tomographic image along said main scanning direction is formed based on the formed image in the depth-wise direction for each of said incident positions, whereby said tomographic image at each of two or more positions along said sub scanning direction is formed, and wherein said accumulated image generating part accumulates said tomographic images at said two or more positions in the depth-wise direction, respectively, thereby generating said accumulated image.

10. A fundus observation device according to claim 1, wherein said first image forming part comprises:
   an illuminating optical system configured to illuminate illumination light on said fundus oculi; and
   an imaging optical system configured to receive fundus reflection light of said illuminated illumination light, and
   wherein it is a fundus camera configured to form the two-dimensional image of the surface of said fundus oculi based on said received fundus reflection light.

11. An ophthalmologic image processing unit that is connected to a first image forming part configured to form a two-dimensional image of a surface of a fundus oculi of an eye and to a second image forming part configured to form a tomographic image in a region of the surface of said fundus oculi corresponding to at least part of said two-dimensional image, the ophthalmologic image processing unit comprising:
   an accumulated image generating part configured to generate an accumulated image by accumulating the tomographic images formed by said second image forming part in a depth-wise direction;
   an extracting part configured to extract a first vascular territory corresponding to a fundus oculi vessel from said two-dimensional image formed by said first image forming part, and extract a second vascular territory corresponding to a fundus oculi vessel from said accumulated image generated by said accumulated image generating part;
   an alignment part configured to align said extracted first vasular territory with said extracted second vascular territory; and
   a specification part configured to specify a layer region or a boundary region between layer regions below the second vascular territory among regions of the tomographic images indicated by the first vascular territory, as a position of a vascular off region below a cross section of a fundus oculi vessel in the tomographic image when said extracted first vascular territory corresponds to said extracted second vascular territory as a result of the alignment.

12. A computer readable medium having computer readable code embodied therein for causing a computer system to perform a predetermined process, the computer connected to a first image forming part configured to form a two-dimensional image of a surface of a fundus oculi of an eye and to a second image forming part configured to form a tomographic image in a region of a surface of said fundus oculi corresponding to at least part of said two-dimensional image, wherein the predetermined process comprising:
   generating an accumulated image by accumulating the tomographic images formed by said second image forming part in a depth-wise direction;
   extracting a first vascular territory corresponding to a fundus oculi vessel from said two-dimensional image formed by said first image forming part, and extracting a second vascular territory corresponding to a fundus oculi vessel from said accumulated image;
   aligning said extracted first vascular territory with said extracted second vascular territory; and
   specifying a layer region or a boundary region between layer regions below the second vascular territory among regions of the tomographic images indicated by the first vascular territory, as a position of a vascular off region below a cross section of the fundus oculi vessel in the tomographic image when said extracted first vascular territory corresponds to said extracted second vascular territory as a result of said aligning step.

13. An ophthalmologic image processing method, comprising the steps of:
   forming a two-dimensional image of a surface of a fundus oculi of an eye;
   forming a tomographic image based on data obtained by scanning a region of the surface of the fundus oculi corresponding to at least part of the two-dimensional image;
   generating an accumulated image by accumulating the tomographic images in a depth-wise direction;
   extracting a first vascular territory corresponding to a fundus oculi vessel from the two-dimensional image;
   extracting a second vascular territory corresponding to the fundus oculi vessel from the accumulated image;
   aligning said extracted first vascular territory with said extracted second vascular territory; and
   specifying a layer region or a boundary region between layer regions below the second vascular territory among regions of the tomographic images indicated by the first vascular territory, as a position of a vascular off region below corresponding to a cross section of the fundus oculi vessel in the tomographic image when said extracted first vascular territory corresponds to said extracted second vascular territory as a result of said aligning step.

* * * * *